United States Patent [19]

Hudspeth et al.

[11] Patent Number: 4,863,905
[45] Date of Patent: Sep. 5, 1989

[54] RENIN INHIBITORS II

[75] Inventors: James P. Hudspeth; James S. Kaltenbronn; Joseph T. Repine; Peter W. K. Woo, all of Ann Arbor, Mich.

[73] Assignee: Warner-Lambert Company, Morris Plains, N.J.

[21] Appl. No.: 11,990

[22] Filed: Feb. 4, 1987

[51] Int. Cl.$^4$ .................. A61K 37/43; C07K 5/06; C07K 5/08
[52] U.S. Cl. ........................ 514/18; 514/19; 530/331
[58] Field of Search .............. 530/330, 331; 514/15, 514/16, 17, 18, 19

[56] References Cited

U.S. PATENT DOCUMENTS

| 4,479,941 | 5/1986 | Veber et al. | 514/17 |
| 4,609,643 | 9/1986 | Szelke et al. | 514/17 |
| 4,661,473 | 4/1987 | Boger et al. | 514/15 |
| 4,663,310 | 5/1987 | Beck et al. | 514/15 |
| 4,668,663 | 5/1987 | Boger et al. | 514/16 |
| 4,668,770 | 5/1987 | Boger et al. | 530/330 |

FOREIGN PATENT DOCUMENTS

85/308759 7/1986 European Pat. Off. .
8403044 8/1984 PCT Int'l Appl. .

Primary Examiner—Delbert R. Phillips
Attorney, Agent, or Firm—Elizabeth M. Anderson

[57] ABSTRACT

The invention concerns novel renin-inhibiting peptides which are modified as isosteres. These peptides are useful for treating renin-associated hypertension and hyperaldosteronism. Processes for preparing the peptides, compositions containing them and methods for using them are included. Also included is a diagnostic test using the peptides to determine the presence of renin-associated hypertension or hyperaldosteronism.

20 Claims, No Drawings

RENIN INHIBITORS II

BACKGROUND OF THE INVENTION

Renin is a natural enzyme which is released into the blood from the kidney. It cleaves its natural substrate, angiotensinogen, releasing a decapeptide, angiotensin I. This is in turn cleaved by converting enzyme in the lung, kidney and other tissues to an octapeptide, angiotensin II. Angiotensin II raises blood pressure both directly by causing arteriolar constriction and indirectly by stimulating release of the sodium-retaining hormone aldosterone from the adrenal gland causing a rise in extracellular fluid volume. Inhibitors of renins have been sought as an agent for control of hypertension and hyperaldosteronism.

The present invention concerns novel peptides which inhibit renin. It also concerns pharmaceutical compositions containing these novel peptides, methods of treating renin-associated hypertension and hyperaldosteronism, as well as the use of the peptides as diagnostic tools, and the methods for preparing the peptides.

U.S. Pat. No. 4,479,941 covers certain renin-inhibitory peptides of the formula

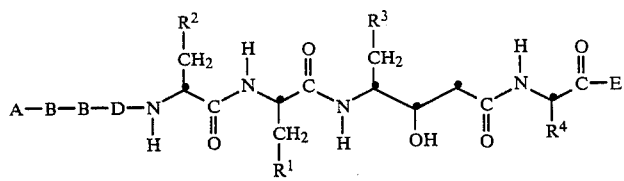

European application No. 85/308759 covers certain renin-inhibitory dipeptides of the formula

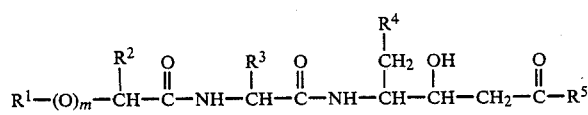

wherein m is 0 or 1 and $R^1$-$R^5$ are a variety of organic groups.

European application No. 184,855 covers renin-inhibitory peptides of the formula

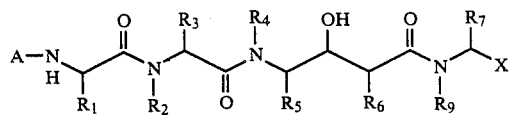

wherein A is an N-protecting group; $R_1$, $R_3$, $R_5$ and $R_7$ are lower alkyl or lipophilic or aromatic amino acid side chains and may be the same or different; $R_2$, $R_4$ and $R_6$ are hydrogen or lower alkyl and may be the same or different; X is hydrogen, lower alkyl or —$CH_2OR_8$, wherein $R_8$ is hydrogen, lower alkyl or alkaryl; and $R_9$ is lower alkyl, hydroxy, hydroxyalkyl, alkoxy, allyl, alkaryloxy or thioalkyl and pharmaceutically acceptable sales thereof.

SUMMARY

The present invention relates to novel peptides of the formula $$ACYL-(A)_n-X-(B)_n-Y-(C)_n-W-(D-)_n-U-(E)_n-V \qquad I$$

and the pharmaceutically acceptable acid addition salts thereof wherein ACYL, n, A, X, B, Y, C, W, D, U, E, and V are defined herein below. The peptides are modified as isosteres in that one or more groups linking two amino acids in the peptide chain X—Y—W—U—V may be replaced by a group or groups selected from A, B, C, D, or E.

The present invention also includes a pharmaceutical composition comprising an effective amount of an above modified peptide of formula I in admixture with a pharmaceutically acceptable carrier or excipient, and a method for treating renin-associated hypertension in a patient suffering therefrom comprising administering to said patient the above pharmaceutical composition in unit dosage form.

Further, the present invention also includes a pharmaceutical composition an effective amount of an above modified peptide of formula I in admixture with a pharmaceutically acceptable carrier or excipient, and a method for treating hyperaldosteronism in a patient suffering therefrom comprising administering to said patient the above pharmaceutical composition in unit dosage form.

The present invention also includes the use of peptides of formula I above as diagnostic tools for the identification of cases of hypertension and hyperaldosteronism due to renin excess.

The invention further includes novel methods for preparing peptides of formula I above.

DETAILED DESCRIPTION

The following table provides a dictionary of the terms used in the description of the present invention.

TABLE I

| Abbreviated Designation | Amino Acid |
|---|---|
| MET | L—METHIONINE |
| MET(O) | L—METHIONINE SULFOXIDE |
| GLN | L—GLUTAMINE |
| GLU | L—GLUTAMIC ACID |
| GLU(OCH2Ph) | L—GLUTAMIC ACID, γ-BENZYL ESTER |

TABLE I-continued

| Abbreviated Designation | Amino Acid |
|---|---|
| GLU(OCH₃) | L—GLUTAMIC ACID, γ-METHYL ESTER |
| GLU(OC₂H₅) | L—GLUTAMIC ACID, γ-ETHYL ESTER |
| GLU(O—t-Bu) | L—GLUTAMIC ACID, γ-t-BUTYL ESTER |
| LYS | L—LYSINE |
| LYS(Z) | L—LYSINE, ε-Z |
| LYS(BOC) | L—LYSINE, ε-BOC |
| LYS(NHC(S)—NHCH₃) | L—LYSINE, ε-N—METHYLTHIOUREA |
| LYS(NHC(O)—NHCH₃) | L—LYSINE, ε-N—METHYLUREA |
| LYS(NHC(O)—NH₂) | L—LYSINE, ε-UREA |
| ORN | L—ORNITHINE |
| ORN(Z) | L—ORNITHINE, δ-Z |
| ORN(BOC) | L—ORNITHINE, δ-BOC |
| ORN(PHT) | L—ORNITHINE, δ-PHTHALOLYL |
| ORN(Ac) | L—ORNITHINE, ε-ACETYL |
| LYS(Ac) | L—LYSINE, ε-ACETYL |
| ALA | L—ALANINE |
| SER | L—SERINE |
| SER(CH₃) | L—SERINE, O—METHYL ETHER |
| SER(C₂H₅) | L—SERINE, O—ETHYL ETHER |
| SER(CH₂Ph) | L—SERINE, O—BENZYL ETHER |
| ASP | L—ASPARTIC ACID |
| ASP(OCH₃) | L—ACID, β-METHYL ESTER |
| ASP(OC₂H₅) | L—ASPARTIC ACID, β-ETHYL ESTER |
| ASP(OCH₂Ph) | L—ASPARTIC ACID, β-BENZYL ESTER |
| ASP(O—t-Bu) | L—ASPARTIC ACID, β-t-BUTYL ESTER |
| ASN | L—ASPARAGINE |
| CYS | L—CYSTEINE |
| SMeCYS | L—CYSTEINE, S—METHYL |
| S(O)MeCYS | L—CYSTEINE, METHYLSULFOXIDE |
| (Me⁵)PHE | PENTAMETHYLPHENYLALANINE |
| NAPHTHYLALA | 1-NAPHTHYLALANINE |
| ARG | L—ARGININE |
| ARG(NO₂) | L—NITROARGININE |
| CYCLOHEXYLALA | CYCLOHEXYLALANINE |
| HIS | L—HISTIDINE |
| LEU | L—LEUCINE |
| STA | 4(S)—AMINO-3(S)—HYDROXY-6-METHYLHEPTANOIC ACID |
| PHSTA | 4(S)—AMINO-3(S)—HYDROXY-5-PHENYLPENTANOIC ACID |
| CYSTA | 4(S)—AMINO-3(S)—HYDROXY-5-CYCLOHEXANEPENTANOIC ACID |
| ILE | L—ISOLEUCINE |
| PHE | L—PHENYLALANINE |
| HOMOPHE | HOMOPHENYLALANINE |
| NLE | NORLEUCINE |
| VAL | L—VALINE |
| GLY | GLYCINE |
| | Protecting Groups |
| Z | BENZYLOXYCARBONYL |
| BOC | TERT-BUTYLOXYCARBONYL |
| TRT | TRITYL |
| | Acyl Groups |
| DNMA | DI-(α-NAPHTHYLMETHYL)ACETYL |
| | Esters with |
| —OCH₃ | METHANOL |
| —OC₂H₅ | ETHANOL |
| | Amides with |
| —NHCH₂CH(CH₃)CH₂CH₃ | 2-METHYLBUTYLAMINE |
| —NHCH(CH₂OH)CH(CH₃)CH₂CH₃ | ISOLEUCINOL |
| —NHCH₂Ph | BENZYLAMINE |
| —NHCH₂CH₂Ph | PHENETHYLAMINE |

TABLE I-continued

| Abbreviated Designation | Amino Acid |
|---|---|
| 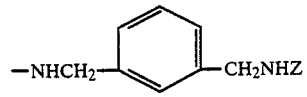 | m-XYLENE-DI-AMINE, Z |
| 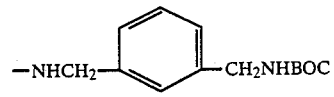 | m-XYLENE-DI-AMINE, BOC |
| 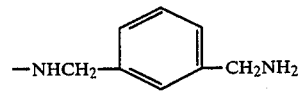 | m-XYLENE-DI-AMINE |
| 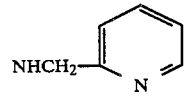 | 2-AMINOMETHYLPYRIDINE |
| 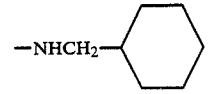 | CYCLOHEXYLMETHYLAMINE |
| $NH_2$ | AMMONIA |
| | *Reagents and Solvents* |
| DCC | N,N'—DICYCLOHEXYL-CARBODIIMIDE |
| HOBT | HYDROXYBENZOTRIAZOLE |
| HOAc | ACETIC ACID |
| EtOAc | ETHYL ACETATE |
| $Et_2O$ | DIETHYL ETHER |
| MeOH | METHANOL |
| TFA | TRIFLUOROACETIC ACID |
| DMF | N,N—DIMETHYLFORMAMIDE |
| TsOH | p-TOLUENESULFONIC ACID |
| $Et_3N$ | TRIETHYLAMINE |
| THF | TETRAHYDROFURAN |
| EtOH | ETHANOL |

In order to describe those compounds where the normal amide bond linking two amino acids has been replaced with other atoms, note the convention of putting the replacing atoms in brackets, while maintaining the usual amino acid abbreviations. For example, when the hydroxyethylene isostere connects ALA and VAL as in the following example,

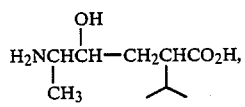

this convention describes this as ALA[CHOHCH$_2$]-VAL. This system is applied in the instant invention in more unusual cases, for example,

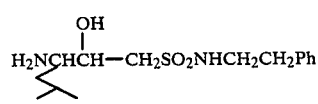

may be written as

The peptides of the present invention are represented by the formula $$\text{ACYL}—(A)_n—X—(B)_n—Y—(C)_n—W—(D)_n—U—(E)_n—V \quad \text{I}$$

or a pharmaceutically acceptable salt thereof, wherein
n is 0 or 1 and the peptide must contain at least 1 link where n is 1;
ACYL is DNMA;
A is —CHOHCH$_2$—;
X is HIS, PHE, HOMOPHE, ARG, ARG(NO$_2$), LEU, ILE, VAL, NLE, MET, MET(O), GLN, GLU, GLU(OCH$_2$Ph), GLU(OCH$_3$), GLU(OC$_2$H$_5$), LYS, LYS(Z), LYS(BOC),

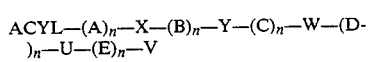

ORN, ORN(Z), ORN(BOC), ORN(PHT), ORN(Ac), LYS(Ac), ALA, SER, SER(CH$_3$), SER(C$_2$H$_5$), SER(CH$_2$Ph), ASP, ASP(OCH$_3$), ASP(OC$_2$H$_5$), ASP-(OCH$_2$Ph), ASP(O-t-Bu), GLU(O-t-Bu), ASN, CYS, SMeCYS, S(O)MeCYS, (Me$^5$)PHE, NAPHTHYLALA, or CYCLOHEXYLALA;
B is —CH$_2$NH—;

Y is STA, PHSTA, CYSTA,

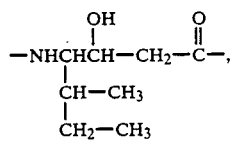

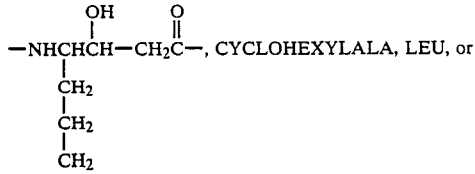, CYCLOHEXYLALA, LEU, or ILE;

C is —CHOHCH₂—, —CH₂SO₂—, —CHOHCHOH—, —CH₂N(BOC)—, or —CH₂NH—;

W is LEU, ILE, NLE, GLY, VAL, or absent;

D is

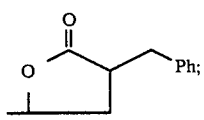

U is LEU, ILE, NLE, VAL, or absent;
E is —CH₂N(BOC)—, —CH₂NH—; and
V is —NHCH₂CH(CH₃)CH₂CH₃, —NHCH(CH₂OH)CH(CH₃)CH₂CH₃, —NHCH₂Ph, —NHCH₂CH₂Ph,

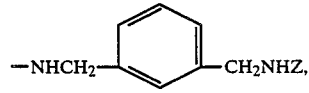

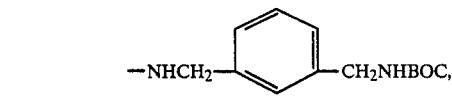

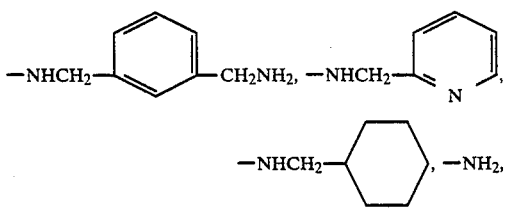

—SO₂—NHCH₂CH₂Ph, —(CH₂)₃CH₃,
—(CH₂)₂CH(CH₃)₂, —(CH₂)₅CH₃, —CH₂OH, or
—CH₂CH(CH₃)CH₂CH₃.

Preferred compounds of the present invention are compounds of formula I wherein:

X is HIS, PHE, HOMOPHE, LEU, ILE, NAPHTHYLALA, ARG(NO₂), or

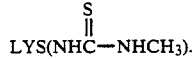.

Other preferred compounds of the present invention are compounds of formula I wherein:

V is —NHCH₂CH(CH₃)CH₂CH₃, —NHCH(CH₂OH)CH(CH₃)CH₂CH₃, —NHCH₂Ph,

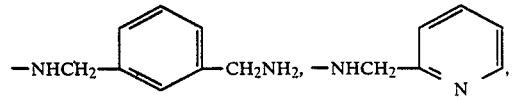

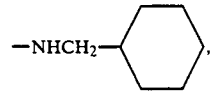,

—SO₂—NHCH₂CH₂Ph, —(CH₂)₃CH₃,
—(CH₂)₂CH(CH₃)₂, —(CH₂)₅CH₃, —CH₂OH, or
—CH₂CH(CH₃)CH₂CH₃.

Particularly valuable compounds within the scope of the invention are:

DNMA—HIS—LEU[CHOHCH₂]SO₂NHCH₂CH₂Ph, DNMA—HIS—LEU[CHOHCH₂]SO₂NHCH₂CH₂Ph(ISOMER),

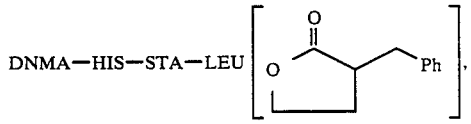,

DNMA—HIS—STA[CH₂SO₂](CH₂)₃CH₃,
DNMA—HIS—CYCLOHEXYLALA[CHOHCH₂](CH₂)₂CH(CH₃)₂, DNMA—HIS—CYCLOHEXYLALA[CHOHCH₂](CH₂)₅CH₃,
DNMA—CYCLOHEXYLALA[CHOHCHOH]CH₂OH, DNMA—HIS[CH₂NH]—STA—NHCH₂CH(CH₃)CH₂CH₃, DNMA—HIS—STA[CH₂N(BOC)]CH₂CH(CH₃)CH₂CH₃,
DNMA—HIS—STA[CH₂NH]CH₂CH(CH₃)CH₂CH₃,
DNMA—HIS—CYCLOHEXYLALA[CHOHCH₂]GLY—LEU—NHCH₂Ph,

DNMA—HIS—CHCLOHEXYLALA[CHOHCH₂]LEU—NHCH₂Ph, DNMA—HIS—CYCLOHEXYLALA[CHOHCH₂]LEU—NHCH₂CH(CH₃)CH₂CH₃,
DNMA—HIS—CYCLOHEXYLALA[CHOHCH₂]GLY—NHCH₂CH(CH₃)CH₂CH₃,

DNMA—HIS—CYCLOHEXYLALA[CHOHCH₂]-GLY—NHCH₂Ph, DNMA—HIS—STA[-CHOHCH₂]CH₂Ph, DNMA—HIS—STA[-CHOHCH₂]CH₂Ph (ISOMER), DNMA[CHOHCH₂]LEU—STA—NHCH₂CH(CH₃)CH₂CH₃, DNMA—LEU—LEU[CHOHCH₂-]SO₂NHCH₂CH₂Ph, DNMA—ARG(NO₂)—LEU[-CHOHCH₂]SO₂NHCH₂CH₂Ph, DNMA—NAPHTHYLALA—LEU[CHOHCH₂]SO₂NHCH₂CH₂Ph, DNMA—ARG(NO₂)—STA—LEU

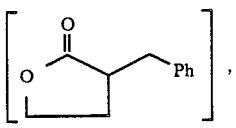

DNMA-LEU-STA-LEU

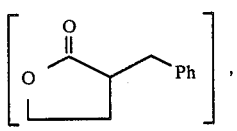

DNMA—PHE—STA[CH₂SO₂](CH₂)₃CH₃, DNMA—NAPHTHYLALA—STA[CH₂SO₂](CH₂)₃CH₃,

DNMA—LYS(NHC̈(=S)—NHCH₃)—STA[CH₂SO₂](CH₂)₃CH₃,

DNMA—ARG(NO₂)—STA[CH₂SO₂](CH₂)₃CH₃, DNMA—LEU—CYCLOHEXYLALA[-CHOHCH₂](CH₂)₂CH(CH₃)₂, DNMA—ILE—CYCLOHEXYLALA[CHOHCH₂](CH₂)₂CH(CH₃)₂, DNMA—NAPHTHYLALA—CYCLOHEXYLALA[CHOHCH₂](CH₂)₅CH₃, DNMA—ARG-(NO₂)—CYCLOHEXYLALA[-CHOHCH₂](CH₂)₅CH₃, DNMA—PHE—CYCLOHEXYLALA[CHOHCHOH]CH₂OH, DNMA—ARG(NO₂)—CYCLOHEXYLALA[-CHOHCHOH]CH₂OH, DNMA—LEU—CYCLOHEXYLALA[CHOHCHOH]CH₂OH, DNMA—LEU[CH₂NH]-STA—NHCH₂CH(CH₃)CH₂CH₃, DNMA—PHE[CH₂NH]STA—NHCH₂CH(CH₃)CH₂CH₃, DNMA—ARG(NO₂)—STA[CH₂N-(BOC)]CH₂CH(CH₃)CH₂CH₃,

DNMA—LYS(NHC̈(=S)—NHCH₃)—STA[CH₂NH]CH₂CH(CH₃)CH₂CH₃,

DNMA—LYS(NHC̈(=S)—NHCH₃)—CYCLOHEXYLALA[CHOHCH₂]GLY—LEU—NHCH₂Ph,

DNMA—LYS(NHC̈(=S)—NHCH₃)—CYCLOHEXYLALA[CHOHCH₂]GLY—ILE—NHCH₂Ph,

DNMA—LEU—CYCLOHEXYLALA[CHOHCH₂]GLY—NHCH₂—⌬—CH₂NH₂,

DNMA—ARG(NO₂)—CYCLOHEXYLALA[CHOHCH₂]GLY—NHCH₂—⌬—CH₂NH₂,

DNMA—HIS—CYCLOHEXYLALA[CHOHCH₂]ILE—NHCH₂—⌬—CH₂NH₂,

DNMA—HIS—CYCLOHEXYLALA[CHOHCH₂]VAL—NHCH₂—⌬—CH₂NH₂,

DNMA—PHE—CYCLOHEXYLALA[CHOHCH₂]LEU—NHCH₂—⌬—CH₂NH₂,

DNMA—HIS—CYCLOHEXYLALA[CHOHCH₂]ILE—NHCH₂Ph,

DNMA—HIS—CYCLOHEXYLALA[CHOHCH2]LEU—NHCH2— 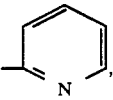,

DNMA—HIS—CYCLOHEXYLALA[CHOHCH2]ILE—NHCH2CH(CH3)CH2CH3,
DNMA—HIS—CYCLOHEXYLALA[CHOHCH2]LEU—NHCH(CH2OH)CH(CH3)CH2CH3,
DNMA—HIS—CYCLOHEXYLALA[CHOHCH2]VAL—NHCH2CH(CH3)CH2CH3,

DNMA—LYS(NHC(=S)—NHCH3)—CYCLOHEXYLALA[CHOHCH2]LEU—NHCH2Ph,

DNMA—ARG(NO2)—CYCLOHEXYLALA[CHOHCH2]LEU—NHCH2— 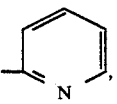,

DNMA—LEU—CYCLOHEXYLALA[CHOHCH2]VAL—NHCH2CH(CH3)CH2CH3,
DNMA—HIS—CYCLOHEXYLALA[CHOHCH2]GLY—NHCH(CH2OH)CH(CH3)CH2CH3,

DNMA—HIS—CYCLOHEXYLALA[CHOHCH2]GLY—NHCH2— 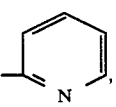,

DNMA—LYS(NHC(=S)—NHCH3)—CYCLOHEXYLALA[CHOHCH2]GLY—NHCH2CH(CH3)CH2CH3,

DNMA—ARG(NO2)—CYCLOHEXYLALA[CHOHCH2]GLY—NHCH2CH(CH3)CH2CH3,

DNMA—LYS(NHC(=S)—NHCH3)—CYCLOHEXYLALA[CHOHCH2]GLY—NHCH2Ph,

DNMA—PHE—STA[CHOHCH2]CH2Ph, DNMA—LEU—STA[CHOHCH2]CH2Ph, DNMA—ARG(NO2)—STA[CHOHCH2]CH2Ph, DNMA—NAPHTHYLALA—STA[CHOHCH2]CH2Ph, DNMA[CHOHCH2]PHE—STA—NHCH2CH(CH3)CH2CH3, DNMA[CHOHCH2]LEU—STA—NHCH2CH(CH3)CH2CH3.

Another aspect of the present invention is a method of preparing a peptide which comprises:

(a) reacting an N-(phenylalkyl)alkyl sulfonamide with n-butyl lithium and Z—LEU—OCH3 in an inert solvent and an inert atmosphere at about −80° forming the corresponding Z—LEU[CHCH2]SO2NH(CH2)$_n$Ph wherein n is an integer of from 2 to 4, (b) reducing the above compound forming a mixtue of Z—LEU[CHOHCH2]SO2NH(CH2)$_n$Ph diastereomers, (c) separating these 2 diastereomers by column chromatography, (d) converting by catalytic hydrogenation each of the 2 diastereomers to the corresponding compound with a free amino terminus, (e) reacting each of the above compounds separately with Z—HIS(TRT) to form the corresponding compound Z—HIS(TRT)—LEU[CHOHCH2]SO2NH(CH2)$_n$Ph, (f) removing by hydrogenation the Z—protecting group from each of the above separately to form HIS(TRT)—LEU[CHOHCH2]SO2NH(CH2)$_n$Ph, (g) reacting each of the above compounds separately with DNMA to form the corresponding DNMA derivative, (h) removing the TRT group from the above DNMA derivative by reacting the derivatives with acetic acid/water to form the desired compounds of the present invention and converting, if desired, to a pharmaceutically acceptable acid addition salt thereof.

Yet another aspect of the present invention is a pharmaceutical composition comprising a renin-inhibitory effective amount of a compound as in formula I above together with a pharmaceutically acceptable carrier.

Still another aspect of the present invention is a method of treating renin-associated hypertension which comprises administering to a mammal a pharmaceutical composition as above.

Another aspect of the invention is a pharmaceutical composition comprising an hyperaldosteronism-inhibitory effective amount of a compound of formula I together with a pharmaceutically acceptable carrier.

Still another aspect of the present invention is a method of treating hyperaldosteronism which comprises administering to a mammal a pharmaceutical composition as above.

Still another aspect of the invention is a method of determining the presence of renin-associated hypertension in a patient which comprises administering to the patient, at a hypotensive dosage level and as a single dose, a peptide of formula I, followed by monitoring of the patient's blood pressure.

The term pharmaceutically acceptable acid addition salt is intended to mean a relatively nontoxic acid addition salt either from inorganic or organic acids such as, for example, hydrochloric, hydrobromic, hydroiodic, sulfuric, phosphoric, acetic, citric, oxalic, malonic, salicyclic, malic, benzoic, gluconic, fumaric, succinic, ascorbic, maleic, tartaric, methanesulfonic and the like. The salts are prepared by contacting the free base form with a sufficient amount of the desired acid to produce a salt in the conventional manner. The free base forms may be regenerated by treating the salt form with a base.

The modified peptides of the present invention possess one or more chiral centers and each center may exist in the R(D) or S(L) configuration. The present invention includes all enantiomeric and epimeric forms as well as the appropriate mixtures thereof.

The peptides of the invention are modified as isosteres in that one or more of the amide groups linking two amino acids in the peptide chain X—Y—W—U—V may be replaced by a group or groups selected from A, B, C, D, or E. The specific replacing groups are enclosed in brackets in the designations of the compounds of this invention.

Some of the above novel peptides may be prepared in accordance with well-known procedures for preparing peptides from their constituent amino acids. Other of the novel peptides of the present invention are prepared by a step-wise procedure or by a fragment coupling procedure depending upon the particular isostere and the particular final product desired. Others were prepared by novel processes detailed below. These processes are merely illustrative and are not intended to be exhaustive.

Scheme I—for Examples 1 and 2

CH₃SO₂NHCH₂CH₂Ph ⟶ Z—LEU[COCH₂]SO₂NHCH₂CH₂Ph ⟶
     1                                           2

Z—LEU[CHOHCH₂]SO₂NHCH₂CH₂Ph (separate fast and ⟶
              3                  slow moving isomer)

LEU[CHOHCH₂]SO₂NHCH₂CH₂Ph ⟶
             4

Z—HIS(TRT)—LEU[CHOHCH₂]SO₂NHCH₂CH₂Ph ⟶
             5

HIS(TRT)—LEU[CHOHCH₂]SO₂NHCH₂CH₂Ph ⟶
             6

DNMA—HIS(TRT)—LEU[CHOHCH₂]SO₂NHCH₂CH₂Ph ⟶
             7

DNMA—HIS—LEU[CHOHCH₂]SO₂NHCH₂CH₂Ph
             8

In Scheme I above, N-phenethylmethanesulfonamide (1) is reacted with n-butyl lithium and then with Z-LEU-OCH, in an inert solvent in an inert atmosphere at very low temperatures to produce Z-LEU[COCH₂]SO₂NHCH₂CH₂Ph (2). The reaction takes about three hours. Compound (2) is reduced with sodium borohydride to form a mixture of Z-LEU[CHOHCH₂]SO₂NCH₂CH₂Ph diastereomers (3). This reaction occurs in ethanol at room temperature over a period of about 2 to 48 hours.

The diastereomers are separated by chromatography on a silica gel column into a fast and slow moving component. The two isomers are each treated separately according to the following sequence of reactions.

The Z-protected compound (3) is converted into the corresponding compound (4) by catalytic hydrogenation over Pd/BaSO₄ in MeOH. Compound (4) is reacted with Z—HIS(TRT) in the presence of hydroxybenzotriazole and dicyclohexylcarbodiimide to form the corresponding Z-protected compound (5). The Z group is removed by hydrogenation of compound (5) forming HIS(TRT)-LEU[CHOHCH₂]SO₂NHCH₂CH₂Ph (6). Compond (6) is reacted with di-(α-naphthylmethyl) acetic acid to form the DNMA derivative (7). The TRT group is then removed by reaction of compound (7) with acetic acid/water forming the desired product (8) as in Example 1.

Scheme II—for the modified portion of Example 4

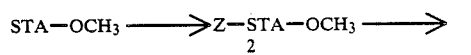

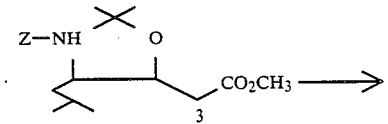

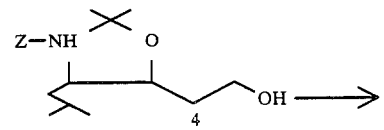

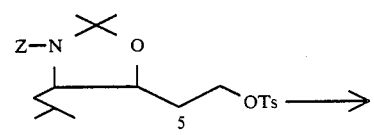

-continued

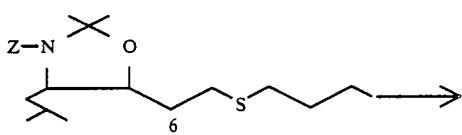

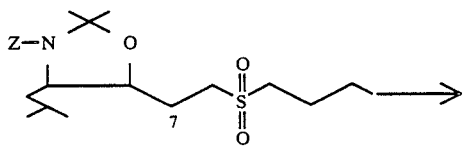

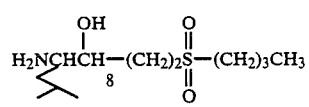

In above Scheme II the hydrochloride salt of STA—OCH₃ is neutralized and reacted with benzyl chloroformate forming compound (2). This is then reacted with 2,2-dimethoxypropane using a catalytic amount of p-toluenesulphonic acid to form compound (3). The reaction proceeds in about two hours at reflux. Compound (3) is then reduced at the ester group to the corresponding alcohol (4) with lithium borohydride. The reaction runs 1 to 12 hours at about 0°–25°. The alcohol (4) is converted to the tosylate (5) and this compound is then reacted with 1-butanethiol at low temperatures for about twenty-four hours in liquid ammonia to form the corresponding thioether (6). The thioether is oxidized to the corresponding sulfone (7) using a peracid such as m-chloroperoxybenzoic acid. The reaction occurs in an inert solvent such as methylene chloride at about 25° in about 1–4 hours. The compound is then catalytically hydrogenated with, for example, palladium on charcoal, at room temperature to the corresponding compound with a free amino terminus (8). Desired compounds of the present invention are then prepared in a manner analogous to the final steps of Scheme I above.

Scheme III—for the modified portion of Examples 5–7

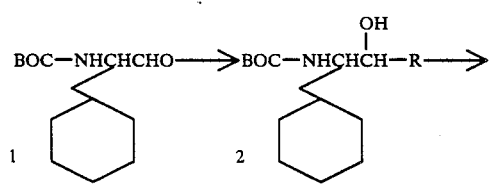

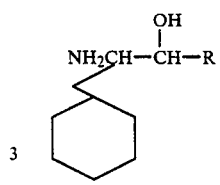

In Scheme III above BOC—CYCLOHEXYLALA[-CHO] (1) in a cooled solution of diethyl ether is reacted with an alkyl Grignard reagent to prepare the corresponding

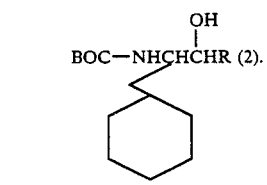

Preferred reagents are, for example, 4-methylheptyl magnesium bromide, n-heptylmagnesium bromide, or vinylmagnesium bromide. Compound (2) in an inert solvent such as methylene chloride is then treated with anhydrous HCl gas forming the corresponding compound with a free amino terminus (3). Desired compounds of the present invention are then prepared in a manner analogous to the final steps of Scheme I above. For Example 7, modified intermediate (3) (R=vinyl) is converted according to the final steps of Scheme I to Z—HIS(TRT)

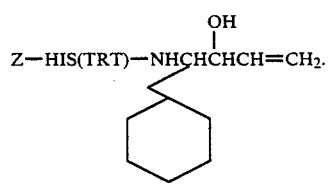

This compound is then reacted with osmic acid in dioxane at about room temperture for 1–4 days to form the triol,

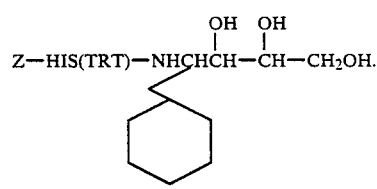

Removal of the Z-group, adding di-(α-naphthylmethyl) acetic acid, and final removal of the trityl group then proceeds as outlined in the final steps of Scheme I.

Scheme IV—for the modified portion of Examples 9 and 10

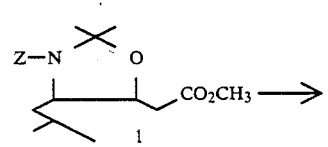

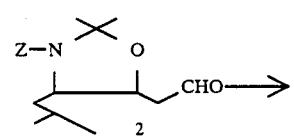

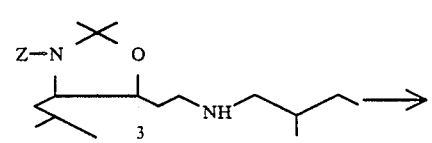

-continued

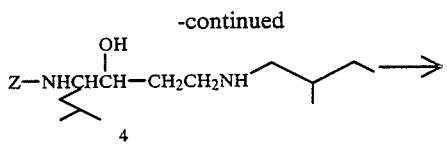
4

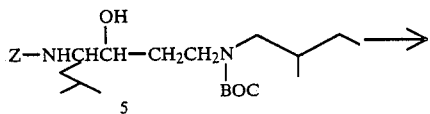
5

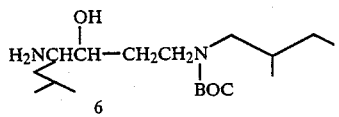
6

In Scheme IV above Z—N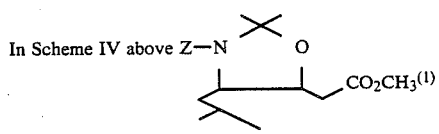

in toluene is cooled to −55° and reacted with diisobutylaluminumhydride to form the corresponding aldehyde (2). A solution of S-2-methylbutylamine and compound (2) in dry THF is stirred overnight in the presence of activated 3A molecular sieves and then treated with NaCNBH₃ to form a secondary amine (3). This compound is treated with a strong acid like TFA at room temperature for 0.5–1 hour, removing the ketal-protecting group and forming the Z-derivative (4). This compound is reacted with di-t-butyldicarbonate forming the BOC-protected compound (5). A solution of compound (5) in methanol is hydrogenated in the presence of a catalyst, preferably palladium on charcoal, to remove the Z-group forming (6). The reaction sequence then follows in a manner analogous to the final steps in Scheme I to produce the desired compounds of the present invention.

Scheme V—for the hydroxyethyl isosteres in Examples 11–17

Example 20 is prepared in an analogous manner.

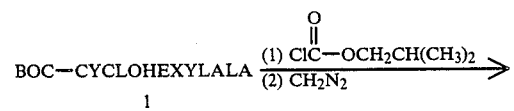
1

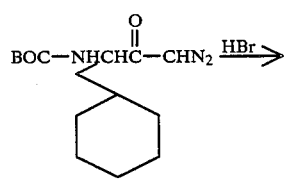
2

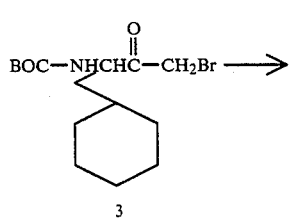
3

-continued

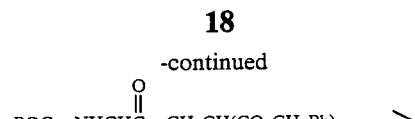
4

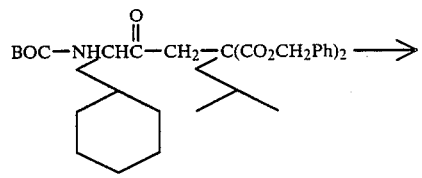
5

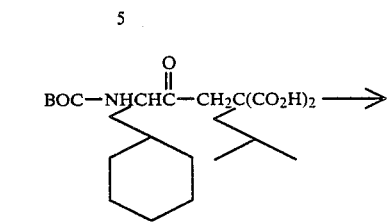
6

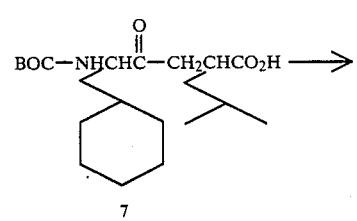
7

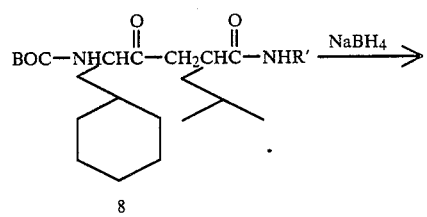
8

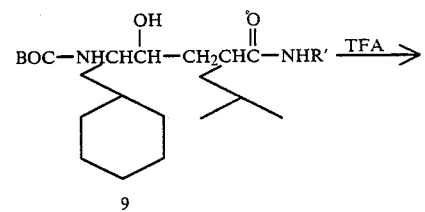
9

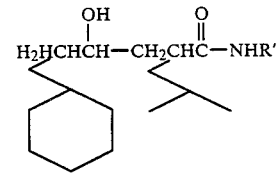
10

In Scheme V above BOC—CYCLOHEXYLALA (1) is reacted with an alkylhaloformate and diazomethane in an inert solvent such as ethylacetate forming BOC—CYCLOHEXYLALA[COCHN₂] (2). The reaction is carried out at temperatures between −10° and +10° for from about 10 to 30 hours. The preferred reaction conditions are about 0° and about ten hours.

Compound (2) is brominated with hydrogen bromide in ether to form BOC—CYCLOHEXYLALA[COCH$_2$Br] (3). This reaction is carried out at temperatures of from −10° to −30°, preferably at about −20°.

Compound (3) is reacted with a malonic acid diester and sodium hydride to form compound (4). The reaction takes place in an inert solvent such as DMF, THF, or DMSO at about room temperature for about 24 hours.

To compound (4) in, for example, DMSO, sodium hydride and isobutyl iodide are added at about 20°–30°. The reaction runs for about ten to thirty hours, preferably about 24 hours, forming compound (5).

Removing the ester groups of compound (5) with hydrogen in the presence of Pd/carbon gives compound (6). This reaction takes about 3 to 24 hours and occurs at about room temperature.

Dissolving compound (6) in toluene and heating at reflux for 3 to 6 hours gives compound (7).

Compound (7) is reacted with a primary amine in the presence of DCC to form the corresponding compound (8). The reaction occurs in an inert solvent such as DMF at room temperature for about 24 hours.

Compound (8) is reduced by reaction with sodium borohydride to form compound (9) which is then reacted with TFA to remove the protecting BOC group and form compound (10) with a free amino terminus.

Scheme VI—for the hydroxyethyl isostere in Examples 18 and 19

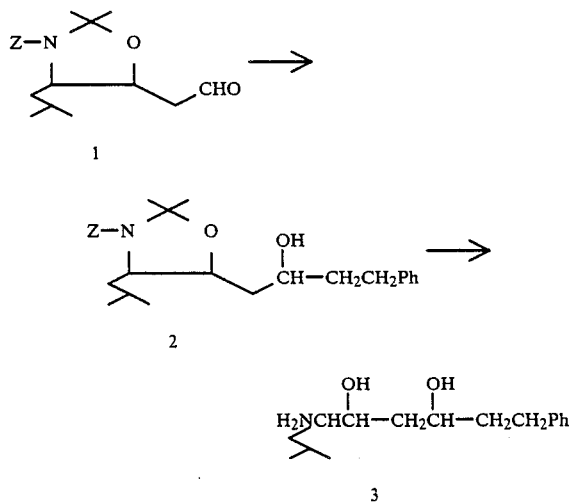

In Scheme VI above compound (1) undergoes a Grignard reaction with an (ω-haloalkyl)benzene to form a compound of type (2) above. The reaction takes place in an anhydrous inert solvent over a period of about two hours.

The ring in compound (2) is opened during catalytic hydrogenation, for example with a palladium/carbon catalyst, to form compound (3).

The strategy of peptide chain assembly and selection and removal of protecting groups is discussed in Chapter 1, "The Peptide Bond," in "The Peptides. Analysis, Synthesis, Biology," E. Gross and J. Meienhofer, Eds., Academic Press, New York, NY, 1979, Vol. 1, pp. 42–44.

The DCC/HOBT method of coupling is well-known to those skilled in the art and is discussed in Chapter 5, "The Carbodiimide Method" by D. H. Rich and J. Singh in "The Peptides. Analysis, Synthesis, Biology," E. Gross and J. Meienhofer, Eds. Academic Press, New York, NY, 1979, Vol. 1, pp. 241–261.

Peptide coupling depends on activating the carboxyl group of the protected amino acid prior to condensing it with another peptide containing a free amino terminus. In addition to the DCC coupling method described above, other methods of activating the carboxyl group of a protected amino acid include:

(1) The azide method—described in Chapter 4 of the above reference.

(2) The mixed anhydride method—described in Chapter 6 of the above reference.

(3) The active ester method—described in Chapter 3 of the above reference.

The compounds of the present invention are useful for treating renin-associated hypertension and hyperaldosteronism. They are also useful as diagnostic tools for determining the presence of renin-associated hypertension or hyperaldosteronism.

Pharmaceutical compositions which comprise an effective amount of the compound in combination with a pharmaceutically acceptable carrier are part of the present invention. An important aspect of the present invention is a method of treating renin-associated hypertension in a mammal which comprises administering a pharmaceutical composition containing an effective amount of a compound of the invention in combination with a pharmaceutically acceptable carrier to the mammal.

The effectiveness of the aforementioned compound is determined by a test for in vitro renin inhibitory activity. This activity is determined by a standard radioimmunoassay for angiotensin I. In this assay the enzyme, renin, incubated for two hours at 37° in the presence of a substrate, angiotensinogen, generates the product, angiotensin I. Test compounds are added to the incubation mixture. Relative activity is reported as the IC$_{50}$, which is the molar concentration of test compound causing a 50% inhibition of the renin activity.

| Compound | Activity IC$_{50}$ (M) |
|---|---|
| DNMA—HIS—LEU[CHOHCH$_2$]SO$_2$NHCH$_2$CH$_2$Ph | $1.2 \times 10^{-5}$ |
| DNMA—HIS—LEU[CHOHCH$_2$]SO$_2$NHCH$_2$CH$_2$Ph(ISOMER) | |
| 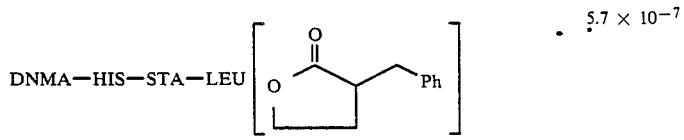 | $5.7 \times 10^{-7}$ |

| Compound | Activity IC$_{50}$ (M) |
|---|---|
| DNMA—HIS—STA[CH$_2$SO$_2$](CH$_2$)$_2$CH(CH$_3$)$_2$ | 1.6 × 10$^{-7}$ |
| DNMA—HIS—CYCLOHEXYLALA[CHOHCH$_2$](CH$_2$)$_2$CH(CH$_3$)$_2$ | 1.8 × 10$^{-6}$ |
| DNMA—HIS—CYCLOHEXYLALA[CHOHCH$_2$](CH$_2$)$_5$CH$_3$ | 9.2 × 10$^{-6}$ |
| DNMA—HIS—CYCLOHEXYLALA[CHOHCHOH]CH$_2$OH | 2.8 × 10$^{-7}$ |
| DNMA—HIS[CH$_2$NH]STA—NHCH$_2$CH(CH$_3$)CH$_2$CH$_3$ | 1.6 × 10$^{-5}$ |
| DNMA—HIS—STA[CH$_2$N(BOC)]CH$_2$CH(CH$_3$)CH$_2$CH$_3$ | 9.9 × 10$^{-6}$ |
| DNMA—HIS—STA[CH$_2$NH]CH$_2$CH(CH$_3$)CH$_2$CH$_3$ | 8.7 × 10$^{-6}$ |
| DNMA—HIS—CYCLOHEXYLALA[CHOHCH$_2$]GLY—LEU—NHCH$_2$Ph | 6.4 × 10$^{-6}$ |
| DNMA—HIS—CYCLOHEXYLALA[CHOHCH$_2$]  | 1.2 × 10$^{-5}$ |
| DNMA—HIS—CYCLOHEXYLALA[CHOHCH$_2$]  | 4.6 × 10$^{-6}$ |
| DNMA—HIS—CYCLOHEXYLALA[CHOHCH$_2$]LEU—NHCH$_2$Ph | 4.4 × 10$^{-6}$ |
| DNMA—HIS—CYCLOHEXYLALA[CHOHCH$_2$]LEU—NHCH$_2$CH(CH$_3$)CH$_2$CH$_3$ | 1.7 × 10$^{-7}$ |
| DNMA—HIS—CYCLOHEXYLALA[CHOHCH$_2$]GLY—NHCH$_2$CH(CH$_3$)CH$_2$CH$_3$ | 2.5 × 10$^{-7}$ |
| DNMA—HIS—CYCLOHEXYLALA[CHOHCH$_2$]GLY—NHCH$_2$Ph | 3.4 × 10$^{-6}$ |
| DNMA—HIS—STA[CHOHCH$_2$]CH$_2$Ph | 1.2 × 10$^{-5}$ |
| DNMA—HIS—STA[CHOHCH$_2$]CH$_2$Ph (ISOMER) | 1.4 × 10$^{-6}$ |
| DNMA[CHOHCH$_2$]LEU—STA—NHCH$_2$CH(CH$_3$)CH$_2$CH$_3$ | 1.9 × 10$^{-6}$ |

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders or tablet disintegrating agents; it can also be encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 50 to 10 to about 70 percent of the active ingredient. Suitable solid carriers are magnesium carbonate, magnesium stearate, talc, sugar, lactose, pectin, dextrin, starch, gelatin, tragacanth, methylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

For preparing suppositories, a low melting wax such as a mixture of fatty acid glycerides or cocoa butter is first melted, and the active ingredient is dispersed homogeneously therein by stirring. The molten homogeneous mixture is then poured into convenient sized molds, allowed to cool, and thereby solidify.

Liquid form preparations include solutions, suspensions, and emulsions. As an example may be mentioned water or water/propylene glycol solutions for parenteral injection. Liquid preparations can also be formulated in solution in aqueous polyethyleneglycol solution. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid from preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like, as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself, or it can be the appropriate number of any of these in packaged form.

The quantity of active compound in a unit dose of preparation may be varied or adjusted from 1 mg to 500 mg, preferably 5 to 100 mg according to the particular application and the potency of the active ingredient. The compositions can, if desired, also contain other compatible therapeutic agents.

In therapeutic use as renin inhibitors, the mammalian dosage range for a 70 kg subject is from 1 to 1500 mg/kg of body weight per day or preferably 25 to 740 mg/kg of body weight per day optionally in divided portions. The dosages, however, may be varied depending upon the requirements of the patient, the severity of the conditions being treated, and the compound being employed. Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

The following examples are provided to enable one skilled in the art to practice the present invention. These examples are not intended to limit the scope of the invention, rather they are illustrations thereof.

EXAMPLE 1

DNMA—HIS—LEU[CHOHCH$_2$]SO$_2$NHCH$_2$CH$_2$Ph

A solution of 137 mg (0.135 mmole) of DNMA—HIS(TRT)—LEU[CHOHCH$_2$]SO$_2$NHCH$_2$CH$_2$Ph in 13 ml of 80% acetic acid was heated at 92°-94° for five minutes, then cooled. The solution was evaporated in vacuo, dissolved in 3 ml of water and again evaporated to dryness. The residue was dissolved in hexane-chloroform (1:1) and chromatographed on silica gel. Trityl alcohol was eluted with CHCl$_3$ and the product was eluted with 10% MeOH in CHCl$_3$. Combining the appropriate fractions using CH$_2$Cl$_2$ gave 101.4 mg of pure product, mp 104°-114°.

Calcd. for C$_{45}$H$_{51}$N$_5$O$_5$S.0.4CH$_2$Cl$_2$: C, 67.49; H, 6.46; N, 8.67. Found: C, 67.60; H, 6.54; N, 8.55.

The structure was also confirmed by FAB mass spectroscopy.

EXAMPLE 2

DNMA—HIS—LEU[CHOHCH$_2$]SO$_2$NHCH$_2$CH$_2$Ph (Isomer)

A solution of 123 mg of DNMA—HIS(TRT)—LEU[CHOHCH$_2$]SO$_2$NHCH$_2$CH$_2$Ph in 12 ml of 80% aqueous acetic acid was heated at 92°-94° with good stirring for five minutes, allowed to stand at ambient temperature for one minute, and cooled to 25°. The solution was evaporated in vacuo, dissolved in water and again evaporaed to give 140 mg of residue. The residue was dissolved in chloroform-hexane (1:1) and chromatographed on silica gel. After elution of trityl alcohol with CHCl$_3$, the pure product was eluted with 10% MeOH in CHCl$_3$. Combing the appropriate fractions using CH$_2$Cl$_2$ gave 98 mg of the purified product as a white solid.

Calcd. for C$_{45}$H$_{51}$N$_5$O$_5$S.0.4CH$_2$Cl$_2$: C, 67.49; H, 6.46; N, 8.67. Found: C, 67.35; H, 6.67; N, 8.62.

The structure was also confirmed by the FAB mass spectrum.

EXAMPLE 3

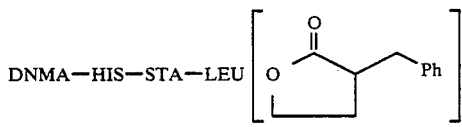

A solution of 104 mg of

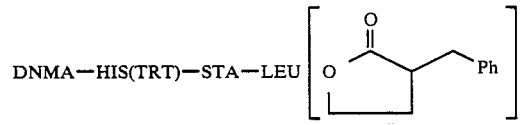

in 9 ml of 80% aqueous acetic acid was heated for five minutes, at 92°-94°, allowed to stand at room temperature for two hours, and evaporated to dryness in vacuo. A few ml of water was added and evaporation was repeated. The residue was chromatographed on silica gel. Trityl alcohol was eluted with hexane:chloroform (1:1), and the product was eluted with 0.5% MeOH in CHCl$_3$. Combining the appropriate fractions with the aid of CH$_2$Cl$_2$ gave 59.7 mg of the product as a solid.

Calcd. for C$_{54}$H$_{63}$N$_5$O$_6$.0.3CH$_2$Cl$_2$: C, 72.17; H, 7.10; N, 7.75. Found: C, 72.34; H, 7.18; N, 7.78.

The structure was also confirmed by the FAB mass spectrum.

EXAMPLE 4

DNMA—HIS—STA[CH$_2$SO$_2$](CH$_2$)$_3$CH$_3$

DNMA—HIS(TRT)—STA[CH$_2$SO$_2$](CH$_2$)$_3$CH$_3$ (0.36 g, 0.37 mmole) was dissolved in 5 ml of 80% HOAc and heated on a steam bath for five minutes. After cooling to 25° for 1.5 hour, the HOAc was removed in vacuo, and the residue was taken up in EtOAc and washed with brine to which had been hadded enough 2N NaOH to bring the pH to 10. The organic phase was again washed with brine, dried over MgSO$_4$, and filtered. The filtrate was reduced in volume in vacuo and then added to excess Et$_2$O. The precipitated solid was collected and washed with Et$_2$O to give 0.2 g of product. The structure was confirmed by NMR and mass spectral analysis.

Calcd. for C$_{42}$H$_{52}$N$_4$O$_5$S.0.25CHCl$_3$ (MW 754.81): C, 67.23; H, 6.97; N, 7.42; S, 4.24. Found: C, 67.36; H, 7.00; N, 7.06; S, 4.56.

EXAMPLE 5

DNMA—HIS—CYCLOHEXYLALA[-CHOHCH$_2$](CH$_2$)$_2$CH(CH$_3$)$_2$

DNMA—HIS(TRT)—CYCLOHEXYLALA[-CHOHCH$_2$](CH$_2$)$_2$CH(CH$_3$)$_2$ (1.80 g, 1.91 mmole) was dissolved in 20 ml 80% HOAc and heated on a steam bath for six minutes. After cooling to 25° over 45 minutes, the solvent was removed in vacuo and the residue was dissolved in EtOAc. The solution was washed with 1N NaOH and brine. The organic phase was dried over MgSO$_4$, filtered, and stripped to a foam, 1.79 g. The foam was chromatographed on 50 g silica gel eluting with 20/80 MeOH/EtOAc to give a white foam, 1.32 g. Spectra and elemental analyses confirmed the proposed structure.

Calcd. for C$_{45}$H$_{56}$N$_4$O$_3$.0.25C$_4$H$_8$O$_2$ (MW 722.99): C, 77.11; H, 8.05; N, 7.99. Found: C, 76.62; H, 7.85; N, 7.79.

Rotation: $[\alpha]_D^{23} = -59.9°$ (C, 1.22, MeOH).

EXAMPLE 6

DNMA—HIS—CYCLOHEXYLALA[-CHOHCH$_2$](CH$_2$)$_5$CH$_3$

DNMA—HIS(TRT)—CYCLOHEXYLALA[-CHOHCH$_2$](CH$_2$)$_5$CH$_3$ (2.3 g, 2.4 mmole) was dissolved in 20 ml 80% HOAc and heated on a steam bath for six minutes. After cooling to 25° over 45 minutes, the solvent was removed in vacuo and the residue was dissolved in EtOAc. The solution was washed with 1N NaOH and brine. The organic phase was dried over MgSO$_4$, filtered, and stripped to a foam, 2.33 g. The foam was chromatographed on silica gel eluting with 20/80 MeOH/EtOAc, giving a white foam, 1.61 g. Spectra and elemental analyses confirmed the structure.

Calcd. for C$_{46}$H$_{58}$N$_4$O$_3$.0.125C$_4$H$_8$O$_2$ (MW 726.01): C, 76.93; H, 8.19; N, 7.72. Found: C, 77.07; H, 8.06; N, 7.72.

Rotation: $[\alpha]_D^{23} = -58.4°$ (C, 1.04, MeOH).

EXAMPLE 7

DNMA—HIS—CYCLOHEXYLALA[CHOHCHOH]CH$_2$OH

DNMA—HIS(TRT)—CYCLOHEXYLALA[-CHOHCHOH]CH$_2$OH (0.81 g, 0.88 mmole) was dissolved in 12 ml 80% HOAc and heated on a steam bath for four minutes. After cooling to 25° over 30 minutes, the solvent was removed in vacuo and the residue was taken up into H$_2$O and stripped again. The residue was partitioned between H$_2$O and EtOAc. The organic phase was reduced in volume in vacuo and added to excess Et$_2$O. The precipitated solid was filtered, washed with Et$_2$O and dried to give a grey solid, 0.33 g. Spectral and elemental analyses confirmed the structure.

Calcd. for C$_{41}$H$_{48}$N$_4$O$_5$.0.5HOAc (MW 706.89): C, 71.36; H, 7.13; N, 7.93. Found: C, 71.23; H, 6.89; N, 8.09.

EXAMPLE 8

DNMA—HIS[CH$_2$NH]-STA—NHCH$_2$CH(CH$_3$)CH$_2$CH$_3$

DNMA—HIS(TRT)[CH$_2$N(BOC)]-STA—NHCH$_2$CH(CH$_3$)CH$_2$CH$_3$ (2.16 g, 2.09 mmole) was dissolved in a mixture of 35 ml CH$_2$Cl$_2$ and 10 ml TFA. After 40 minutes, the mixture was stripped to an oil and triturated with 1N NaOH, giving a white gum. The aqueous phase was decanted, and the gum was dissolved in EtOAc. The organic phase was washed with brine, dried over MgSO$_4$, filtered, and stripped to a foam. The foam was dissolved in 20 ml 80% HOAc and was heated on a steam bath for five minutes. After cooling to 25° over 30 minutes, the solvent was removed in vacuo, and the residue was dissolved in EtOAc/H$_2$O. The pH was adjusted to 12 with 5N NaOH, and the organic phase was washed with brine, dried over MgSO$_4$, filtered, and stripped to a foam. The foam was chromatographed on silica gel, eluting with a gradient of 0 to 20% MeOH in CHCl$_3$. The product was recovered as a foam, 0.62 g. Spectral and elemental analyses confirmed the structure.

Calcd. for C$_{43}$H$_{55}$N$_5$O$_3$ (MW 689.95): C, 74.86; H, 8.03; N, 10.15. Found: C, 74.33; H, 8.04; N, 10.07.

Rotation: $[\alpha]_D^{23} = -10.1°$ (C, 1.148, MeOH).

EXAMPLE 9

DNMA—HIS—STA[CH$_2$N-(BOC)]CH$_2$CH)CH$_3$)CH$_2$CH$_3$

DNMA—HIS(TRT)—STA[CH$_2$N-(BOC)]CH$_2$CH(CH$_3$)CH$_2$CH$_3$ (2.56 g, 2.48 mmole) was dissolved in 50 ml 80% acetic acid and heated on a steam bath for five minutes. After standing at 25° for one hour, the acetic acid was stripped off in vacuo, and the residue was partitioned between EtOAc and H$_2$O adjusted to pH 8 with 5N NaOH. The organic phase was washed with brine, dried over MgSO$_4$, filtered, and stripped to an oil. The oil was taken up into Et$_2$O, and added to excess hexane. The precipitated solid was filtered and dried to give a white solid, 1.76 g. This solid was redissolved in Et$_2$O, and again precipitated by addition to hexane. The precipitate was collected and dried to give a white solid, 1.46 g. Spectral and elemental analyses confirmed the structure.

Calcd. for C$_{48}$H$_{63}$N$_5$O$_5$ (MW 790.07): C, 72.97; H, 8.04; N, 8.86. Found: C, 72.26; H, 7.89; N, 8.81.

Rotation: $[\alpha]_D^{23} = -44.2°$ (C, 1.02, MeOH).

EXAMPLE 10

DNMA—HIS—STA[CH$_2$NH]CH$_2$CH(CH$_3$)CH$_2$CH$_3$

DNMA—HIS—STA[CH$_2$NH-(BOC)]CH$_2$CH(CH$_3$)CH$_2$CH$_3$ (1.24 g, 1.57 mmole) was dissolved in 10 ml CH$_2$Cl$_2$ and 10 ml TFA. After one hour at 25° the solution was stripped to a brown oil which was taken up into CH$_2$Cl$_2$ and stripped back to an oil. The oil was partitioned between saturated NaHCO$_3$ solution and EtOAc. The organic phase was washed with brine, dried over MgSO$_4$, filtered, and stripped to an oil. The oil was dissolved in a minimal amount of EtOAc and added to excess Et$_2$O. The precipitated solid was filtered, washed with Et$_2$O, and dried to give a white solid, 0.82 g. Spectral and elemental analyses confirmed the structure.

Calcd. for C$_{43}$H$_{55}$N$_5$O$_3$.0.8CF$_3$CO$_2$H (MW 781.17): C, 68.57; H, 7.20; N, 8.96. Found: C, 68.50; H, 6.91; N, 9.01.

Rotation: $[\alpha]_D^{23} = -52.2°$ (C, 1.11, MeOH).

EXAMPLE 11

DNMA—HIS—CYCLOHEXYLALA[CHOHCH$_2$]-GLY—LEU—NHCH$_2$Ph

DNMA—HIS(TRT)—CYCLOHEXYLALA[-CHOHCH$_2$]GLY—LEU—NHCH$_2$Ph (0.4 g) was dissolved in 80% acetic acid/water (10 ml) and heated on a steam bath for five minutes. The mixture was allowed to cool slowly to 25°. The solvent was evaporated and the residue was extracted with ethyl acetate and sodium carbonate solution. The organic layer was washed with brine, dried iver sodium sulfate, filtered, and evaporated. The residue was eluted from silica gel with chloroform then 10% methanol/chloroform to give 0.26 g of product.

Calcd. for $C_{55}H_{66}N_6O_5.0.5CH_3OH.0.25CHCl_3$: C, 71.45; H, 7.34; N, 8.97. Found: C, 71.08; H, 7.46; N, 9.17.

EXAMPLE 12

(1 g) was dissolved in dichloromethane (50 ml). Trifluoroacetic acid (4 ml) was added and the mixture was stirred for two hours at 25°. The solvent was evaporated and the residue was dissolved in 80% acetic acid/water. The mixture was heaed on a steam bath for five minutes and then allowed to cool slowly to 25°. The solvent was evaporated and the residue was extracted with 10% sodium hydroxide and ethyl acetate. The organic layer was washed with brine, dried over sodium sulfate, filtered, and evaporated. The residue was eluted from silica gel with dichloromethane, then ethyl acetate and then 1:1 ethyl acetate/methanol. Combining the appropriate fractions with the aid of $CH_2Cl_2$ gave 0.6 g of product.

Calcd. for $C_{50}H_{58}N_6O_4.0.6CH_2Cl_2$: C, 70.83; H, 6.96; N, 9.80. Found: C, 70.45; H, 7.05; N, 9.54.

EXAMPLE 13

(0.8 g) was dissolved in dichloromethane and trifluoroacetic acid (4 ml) was added. The mixture was stirred for two hours at 25° and then evaporated to dryness. The residue was dissolved in 80% acetic acid/water and heated on a steam bath for five minutes and then allowed to cool slowly to 25°. The solvent was evaporated and the residue was extracted with ethyl acetate and 10% sodium hydroxide. The organic phase was washed with brine, dried over sodium sulfate, filtered, and evaporated. The residue was eluted from silica gel with ethyl acetate and then 1:1 ethyl acetate/methanol. The fractions were combined in dichloromethane and evaporated to give 0.4 g of product.

Calcd. for $C_{54}H_{66}N_6O_4.0.5CH_2Cl_2$: C, 72.28; H, 7.46; N, 9.28. Found: C, 72.21; H, 7.29; N, 9.02.

EXAMPLE 14

DNMA—HIS—CYCLOHEXYLALA[CHOHCH₂]LEU—NHCH₂Ph

DNMA—HIS(TRT)—CYCLOHEXYLALA[CHOHCH₂]LEU—NHCH₂Ph (0.5 g) was dissolved in 80% acetic acid/water (20 ml). The mixture was heated on a steam bath for five minutes and then allowed to cool slowly to 25°. The solvent was evaporated and the esidue was extracted with ethyl acetate and sodium carbonate solution. The organic phase was washed with brine, dried over sodium sulfate, filtered, and evaporated. The residue was eluted from silica gel with dichloromethane then 10% methanol/ethyl acetate to give 0.3 g of product.

Calcd. for $C_{53}H_{63}N_5O_4.0.125C_4H_8O_2.0.19CH_2Cl_2$: C, 74.87; H, 7.54; N, 8.13. Found: C, 74.78; H, 7.34; N, 7.55.

EXAMPLE 15

DNMA—HIS—CYCLOHEXYLALA[CHOHCH₂]LEU—NHCH₂CH(CH₃)—CH₂CH₃

DNMA—HIS(TRT)—CYCLOHEXYLALA[CHOHCH₂]LEU—NHCH₂—CH(CH₃)CH₂CH₃ (0.5 g) was dissolved in 80% acetic acid/water and heated on a steam bath for five minutes. The mixture was allowed to cool slowly to 25° and then the solvent was evaporated. The residue was extracted with ethyl acetate and sodium carbonate solution. The organic phase was washed with brine, dried over sodium sulfate, filtered, and evaporated. The residue was eluted from silica gel with dichloromethane and then 10% methanol/ethyl acetate to give 0.3 g of product.

Calcd. for $C_{51}H_{67}N_5O_4.0.1C_4H_8O_2.0.07CH_2Cl_2$: C, 74.55; H, 8.27; N, 8.46. Found: C, 74.36; H, 7.95; N, 8.29.

EXAMPLE 16

DNMA—HIS—CYCLOHEXYLALA[CHOHCH₂]-GLY—NHCH₂CH(CH₃)—CH₂CH₃

DNMA—HIS(TRT)—CYCLOHEXYLALA[CHOHCH₂]GLY—NHCH₂—CH(CH₃)CH₂CH₃ (0.85 g) was dissolved in 80% acetic acid/water (20 ml). The mixture was heated on a steam bath for five minutes and then allowed to cool slowly to 25° C. The solvent was evaporated and the residue extracted wtih ethyl acetate and sodium carbonate. The organic phase was washed with brine, dried over sodium sulfate, filtered, and evaporated. The residue was eluted from silica gel with ethyl acetate. Combining the appropriate fractions using dichloromethane gave 0.5 g of product.

Calcd. for $C_{47}H_{59}N_5O_4 \cdot 0.15CH_2Cl_2 \cdot 0.1C_4H_8O_2$: C, 73.26; H, 7.71; N, 8.98. Found: C, 73.45; H, 7.71; N, 9.03.

EXAMPLE 17

DNMA—HIS—CYCLOHEXYLALA[CHOHCH$_2$]-GLY—NHCH$_2$Ph

DNMA—HIS(TRT)—CYCLOHEXYLALA[CHOHCH$_2$]GLY—NHCH$_2$Ph (0.9 g) was dissolved in 80% acetic acid/water (20 ml) and heated on a steam bath for five minutes. The mixture was allowed to cool slowly to 25° C. The solvent was evaporated and the residue extracted with ethyl acetate and sodium carbonate. The organic layer was washed with brine, dried over sodium sulfate, filtered, and evaporated. The residue was eluted from silica gel with chloroform and then 10% methanol/ethyl acetate. The appropriate fractions were combined using dichloromethane to give 0.5 g of product.

EXAMPLE 18

DNMA—HIS—STA[CHOHCH$_2$]CH$_2$Ph

DNMA—HIS(TRT)—STA[CHOHCH$_2$]CH$_2$Ph (1.4 g, 1.45 mmole, fast isomer) was dissolved in 30 ml of 80% HOAc and heated on a steam bath for seven minutes. The mixture was allowed to cool to 25° over 30 minutes and was then stripped in vacuo to an oil. The oil was taken up in EtOAc and 1N NaOH added to neutralize the HOAc present. The EtOAc was washed with brine, dried over MgSO$_4$, filtered, and stripped to a foam. Trituration with Et$_2$O gave 0.64 g of the product as a white solid. The structure was confirmed by NMR and mass spectral analysis.

Calcd. for $C_{46}H_{52}N_4O_4 \cdot 0.5H_2O$ (MW 733.96): C, 75.28; H, 7.28; N, 7.63. Found: C, 75.22; H, 7.29; N, 7.64.

EXAMPLE 19

DNMA—HIS—STA[CHOHCH$_2$]CH$_2$Ph (Isomer)

Treatment of the slower moving isomer (1.4 g, 1.45 mmole) under the conditions described for Example 18 gave 0.84 g of the product as a white foam. The structure was confirmed by NMR and mass spectral analysis.

Calcd. for $C_{46}H_{52}N_4O_4 \cdot 0.5H_2O$ (MW 733.96): C, 75.28; H, 7.28; N, 7.63. Found: C, 75.47; H, 7.25; N, 7.25.

EXAMPLE 20

DNMA[CHOHCH$_2$]LEU—S-TA—NHCH$_2$CH(CH$_3$)CH$_2$CH$_3$

DNMA[COCH$_2$]LEU—S-TA—NHCH$_2$CH(CH$_3$)CH$_2$CH$_3$ (1.16 g, 1.71 mmole) was dissolved in 25 ml anhydrous EtOH. NaBH$_4$ (0.45 g, 0.0119 mole) was added and the mixture was stirred for four hours at 25°. After cooling to 0°, glacial acetic acid was added until the pH to wet test paper indicated 5.5. The solvent was removed in vacuo and the residue was suspended in EtOAc. The suspension was filtered and the filtrate was washed with 1N citric acid, brine, saturated NaHCO$_3$, and brine. The organic phase was dried over MgSO$_4$, filtered, and stripped to give the product as a white foam, 1.12 g. The structure was confirmed by NMR and mass spectral analysis.

Calcd. for $C_{44}H_{60}N_2O_4$ (MW 680.98): C, 77.62; H, 8.88; N, 4.11. Found: C, 76.75; H, 8.86; N, 4.02.

INTERMEDIATES FOR EXAMPLES 1 AND 2

Z—LEU[COCH$_2$]SO$_2$NHCH$_2$CH$_2$Ph

To a solution of 5.98 g (30 mmole) of N-phenethylmethanesulfonamide in 50 ml THF under an argon atmosphere and cooled to −80° was added 33 ml of a 2.4M solution of n-butyl lithium over a 15 minute period. After 1.5 hours at −80°, 4.19 g (15 mmole) of Z—LEU—OCH$_3$ in 4 ml of THF was added dropwise over 0.5 hour. After stirring at −80° for three hours, the mixture was treated with 5 ml of HOAc. The mixture was filtered, the solid washed with THF, and the THF evaporated to give the crude product. This was combined with material from another reaction to give a total of 9.25 g of an oil. This was taken up in EtOAc/hexane and washed with H$_2$O, saturated NaCl solution, and then dried over Na$_2$SO$_4$. Removal of the solvent under reduced pressure gave 8.86 g of a light yellow oil. After chromatography on silica gel, there was obtained 2.3 g of product. Crystallization from Et$_2$O gave 1.25 g of product, mp 66°–72°, $[\alpha]_D^{23} -23.4°$ (C, 1.1, MeOH). FAB mass spectra confirmed the structure.

Z—LEU[CHOHCH$_2$]SO$_2$NHCH$_2$CH$_2$Ph

PREPARATION AND SEPARATION OF DIASTEREOMERS

A solution of 694 mg (1.55 mmole) of Z—LEU[COCH$_2$]SO$_2$NHCH$_2$CH$_2$Ph in 15 ml of absolute EtOH was cooled in ice and treated with 79 mg (2.05 mmole) of NaBH$_4$ and then allowed to stir at room temperature for 44 hours. Glacial HOAc (0.7 ml) was then added and the mixture evaporated under high vacuum to give 1.01 g of crude product. This was taken up in EtOAc and washed with H$_2$O, saturated NaCl solution, and then dried over Na$_2$SO$_4$. Removal of the solvent under reduced pressure left 731 mg of material. This was chromatographed on silica gel using a gradient of 1% MeOH in CHCl$_3$ to 2% MeOH in CHCl$_3$. The material could be separated into 195 mg of a fast moving component and 565 mg of a slow moving component. These were kept separate and provided intermediates for Example 1 and Example 2.

LEU[CHOHCH$_2$]SO$_2$NHCH$_2$CH$_2$Ph (from slow moving diastereomer)

A solution of 565 mg of the slow moving diastereomer of Z—LEU[CHOHCH$_2$]SO$_2$NHCH$_2$CH$_2$Ph in MeOH was stirred under a hydrogen atmosphere with 20% Pd/C until thin layer chromatography indicated complete removal of the Z-protecting group. The reaction mixture was filtered through Celite and the filtrate evaporated under reduced pressure to give 364 mg of product.

Z—HIS(TRT)—LEU[CHOHCH$_2$]SO$_2$NHCH$_2$CH$_2$Ph

A solution of LEU[CHOHCH$_2$]SO$_2$NHCH$_2$CH$_2$Ph (slow isomer, 168 mg, 0.317 mmole), Z—HIS(TRT) (97.5 mg, 0.31 mmole), and hydroxybenzotriazole (44 mg, 0.326 mmole) in 2.5 ml of DMF, was treated at 0° with dicyclohexylcarbodiimide (66.5 mg, 0.319 mmole). After 1.5 hour at 0° the reaction mixture was allowed to stand for 22 hours at room temperature. The reaction mixture was filtered and the filtrate evaporated under reduced pressure to give 418 mg of crude product. This was dissolved in hexane-chloroform (2:1) and chromatographed on silica gel. The appropriate fractions were combined to give 214 mg of the product.

HIS(TRT)—LEU[CHOHCH$_2$]SO$_2$NHCH$_2$CH$_2$Ph

A solution of 265 mg of Z—HIS(TRT)—LEU[CHOHCH$_2$]SO$_2$NHCH$_2$CH$_2$Ph in MeOH was stirred under a hydrogen atmosphere with 20% Pd/BaSO$_4$ until thin layer chromatography indicated complete removal of the Z-protecting group. The reaction mixture was filtered through Celite, and the filtrate evaporated under reduced pressure to give 165 mg of product.

DNMA—HIS(TRT)—LEU[CHOHCH$_2$]SO$_2$NHCH$_2$CH$_2$Ph

To a solution of 138.3 mg (0.199 mmole) of HIS(TRT)—LEU[CHOHCH$_2$]SO$_2$NHCH$_2$CH$_2$Ph, 69.3 mg (0.204 mmole) of di-($\alpha$-naphthylmethyl)acetic acid, and 27.9 mg (0.206 mmole) of hydroxybenzotriazole in 3.0 ml of DMF at 0° was added 42.8 mg (0.205 mmole) of DCC. After stirring for two hours at 0°, the reaction mixture was stirred for 72 hours at room temperature, filtered, and the filtrate evaporated in vacuo to give 280 mg of residue.

The residue was taken up in CHCl$_3$, washed with 1M citric acid solution, satuated NaCl solution, saturated NaHCO$_3$ solution, and again with saturated NaCl solution. After drying over Na$_2$SO$_4$ and removal of the solvent under reduced pressure, there was obtained 251 mg of the crude product as a solid foam.

The crude product was dissolved in hexane/chloroform (1:1) and chromatographed on silica gel, eluting with 1% MeOH in CHCl$_3$. Combining the appropriate fractions gave 160 mg of pure product. The structure was confirmed by the FAB mass spectrum.

LEU[CHOHCH$_2$]SO$_2$NHCH$_2$CH$_2$Ph (from fast moving diastereomer)

A solution of 192 mg of Z—LEU[CHOHCH$_2$]SO$_2$NHCH$_2$CH$_2$Ph, fast moving diastereomer, in MeOH was stirred under a hydrogen atmosphere with 20% Pd/BaSO$_4$ until thin layer chromatography indicated complete removal of the Z-protecting group. The reaction mixture was filtered through Celite and the filtrate evaporated under reduced pressure to give 132 mg of product.

Z—HIS(TRT)—LEU[CHOHCH$_2$]SO$_2$NHCH$_2$CH$_2$Ph (Isomer)

A solution of 132.1 mg (0.42 mmole) of LEU[CHOHCH$_2$]SO$_2$NHCH$_2$CH$_2$Ph, fast isomer, 227.8 mg (0.428 mmole) of Z—HIS(TRT), 57.8 mg (0.427 mmole) of hydroxybenzotriazole in 3.2 ml of DMF was treated at 0° with 89.5 mg (0.429 mmole) of dicyclohexylcarbodiimide. After stirring at 0° for 1.5 hours, the reaction mixture was allowed to stand at room temperature for 31 hours. The mixture was filtered, and the filtrate evaporated in vacuo to give 418 mg of residue. A solution of the residue in CHCl$_3$ was washed twice with saturated NaHCO$_3$ solution, then saturated sodium chloride solution, dried over sodium sulfate, and evaporated to give 438 mg of crude product.

The crude product was dissolved in hexane-chloroform (2:1) and chromatographed on silica gel. Combining the appropriate fractions gave 265 mg of pure product.

HIS(TRT)—LEU[CHOHCH$_2$]SO$_2$NHCH$_2$CH$_2$Ph

A solution of 265 mg of Z—HIS(TRT)—LEU[CHOHCH$_2$]SO$_2$NHCH$_2$CH$_2$Ph in MeOH was stirred under a hydrogen atmosphere with 20% Pd/BaSO$_4$ until thin layer chromatography indicated complete removal of the Z-protecting group. The mixture was filtered through Celite, and the filtrate evaporated under reduced pressure to give 225 mg of product.

DNMA—HIS(TRT)—LEU[CHOHCH$_2$]SO$_2$NHCH$_2$CH$_2$Ph

To a solution of 112.8 mg (0.1626 mmole) of HIS(TRT)—LEU[CHOHCH$_2$]SO$_2$NHCH$_2$CH$_2$Ph, 58.1 mg (0.17 mmole) of di-($\alpha$-naphthylmethyl)acetic acid, and 22.5 mg (0.167 mmole) of hydroxybenzotriazole in 2.4 ml of DMF stirred in an ice bath was added 35.2 mg (0.169 mmole) of dicyclohexylcarbodiimide. After one hour in the ice bath and 46 hours at room temperature, the reaction mixture was filtered and the filtrate evaporated in vacuo at a bath temperature of 30° to give 262 mg of residue. A solution of the residue in CHCl$_3$ was washed with 1M citric acid, saturated NaCl solution, twice with saturated NaHCO$_3$ solution, and again with saturated NaCl solution. After drying over Na$_2$SO$_4$, removal of the solvent gave 215 mg of crude product. The crude product was dissolved in hexane-chloroform (1:1) and chromatographed on silica gel, eluting with 0.5% MeOH in CHCl$_3$. Combining the appropriate fractions gave 137 mg of pure product.

INTERMEDIATES FOR EXAMPLE 3

Z—LEU[COCHN$_2$]

Z—LEU (20 g) and N-methylpiperidine (9.1 ml) were dissolved in dichloromethane (300 ml) and cooled to −20°. Isobutyl chloroformate (9.8 ml) was added dropwise and the mixture stirred for ten minutes after the addition was complete. The mixture was filtered under nitrogen into a cold flask and diazomethane (6 g) in ether added. The mixture was left to stand at 0° overnight. A nitrogen stream was bubbled through the solution to remove any diazomethane. The solvent was evaporated and the residue recrystallized from isopropyl ether/hexane to give 16 g of product, the diazoketone derived from Z—LEU.

Z—LEU[COCH$_2$Br]

The diazoketone (15 g) was dissolved in ether (200 ml) and cooled to −20°. Gaseous hydrogen bromide was bubbled in until the pH of the solution was acidic when tested with litmus paper. The solvent was evaporated to give the product (16 g) as an oil.

Z—LEU[COCH$_2$CH(CO$_2$—t—Bu)$_2$]

Sodium hydride (1.81 g) (60%) was washed with hexane and then suspended in dimethylformamide (10 ml). The mixture was cooled to 0° and di-t-butylmalonate (9.79 g) was added. The mixture was stirred for one hour then was treated with a solution of the bromoketone (15.5 g) in dimethylformamide (30 ml). The mixture was allowed to warm to 25° and was stirred for three hours. 1N citric acid was added and the mixture was extracted with ether. The ether was washed with water, saturated NaHCO$_3$, and then saturated NaCl. After drying over sodium sulfate, the solvent was evaporated. The residue was recrystallized from hexane to give 12 g of product, mp 81°–82°.

Z—LEU[COCH$_2$]PHE[(CO$_2$—t—Bu)$_2$]

Sodium hydride (60% in mineral oil, 625 mg) was washed with n-pentane under argon; 4.5 ml of DMF was then added. The mixture was stirred in an ice bath, and a solution of 7.45 g of Z—LEU[COCH$_2$CH(CO$_2$—t—Bu)$_2$] in 9 ml of DMF was added dropwise with good stirring during one hour, followed by another 11 ml of DMF. After stirring for an additional five hours, the mixture was cooled to −8° and 2.95 g of benzyl bromide was added dropwise with stirring. The mixture was then stirred in an ice bath overnight and a solution of 0.4 ml of glacial acetic acid in 50 ml of EtOAc was added.

The mixture was diluted with EtOAc and washed with H$_2$O, then saturated NaCl solution. Drying over Na$_2$SO$_4$ and removal of the solvent under reduced pressure left 10.2 g of the crude product as an oil. After chromatography on silica gel, eluting with 10% EtOAc in hexane, the appropriate fractions were combined and recrystallized from pentane to give 6.87 g of pure product, mp 71°–77°, $[\alpha]_D^{23} = -20.8°$ (C, 1.06, MeOH).

Z—LEU[COCH$_2$]PHE[(CO$_2$H)$_2$]

A solution of 10.6 g of Z—LEU[COCH$_2$]PHE[(CO$_2$—t—Bu)$_2$] in 80 ml of TFA was allowed to stand at room temperature for 50 minutes and was then evaporated under reduced pressure. Toluene was then added and the solution again evaporated. The residue was then taken up in CHCl$_3$ and washed four times with H$_2$O. After drying over Na$_2$SO$_4$, the solvent was removed under reduced pressure to give 9.33 g of product.

Z—LEU[COCH$_2$]PHE

A solution of 9.3 g of Z—LEU[COCH$_2$]PHE[(CO$_2$H)$_2$] in 130 ml of toluene was heated at reflux for 0.5 hr. The solvent was removed under reduced pressure leaving 8.12 g of crude product. Chromatography on silica gel, eluting with a gradient of CHCl$_3$ to 4% MeOH in CHCl$_3$ gave 5.35 g of pure product.

Z—LEU[COCH$_2$]PHE—NHCH$_2$Ph

To a solution of 1.38 g (3.356 mmole) of Z—LEU[COCH$_2$]PHE in DMF was added 481 mg (3.4 mmole) of hydroxybenzotriazole followed by 372 mg of benzylamine. The solution was cooled in ice and treated with 711 mg (3.4 mmole) of DCC in DMF. After two hours at 0°, the solution was allowed to warm to room temperature. After three days, the mixture was filtered and the filtrate evaporated under reduced pressure. The residue was taken up in EtOAc-hexane and washed with 1M citric acid, brine, saturated NaHCO$_3$ solution, and again with brine. Drying over MgSO$_4$ and removal of the solvent under reduced pressure left 1.66 g of a yellow oil. Trituration with Et$_2$O/hexane gave 1.16 g of the product as a solid.

Z—LEU[CHOHCH$_2$]PHE—NHCH$_2$Ph

A solution of 1.08 g Z—LEU[COCH$_2$]PHE—NHCH$_2$Ph in 48 ml of absolute EtOH was cooled in ice and treated with 245 mg of NaBH$_4$ and allowed to stir at room temperature overnight. Glacial acetic acid (1.5 ml) was added and the mixture evaporated to dryness under reduced pressure. The residue was taken up in CHCl$_3$, washed with 4N acetic acid, saturated NaHCO$_3$ solution, and then brine, and then was dried over MgSO$_4$. Removal of the solvent under reduced pressure left 1.08 g of crude product. Chromatography on silica gel, eluting with 5% THF in CHCl$_3$ gave 498 mg of the slow moving diastereomer.

LEU[CHOHCH$_2$]PHE—NHCH$_2$Ph

A solution of 498 mg of Z—LEU[CHOHCH$_2$]PHE—NHCH$_2$Ph in 8 ml MeOH and 2 ml THF was treated with 50 mg of 20% Pd/BaSO$_4$ and a stream of hydrogen bubbled through the mixture for six hours. The mixture was filtered and the filtrate evaporated under reduced pressure to give 412 mg of product.

BOC—STA—LEU[CHOHCH$_2$]PHE—NHCH$_2$Ph

To a cold solution of 149 mg (0.541 mmole) of BOC—STA, 199 mg (0.541 mmole) of LEU[CHOHCH$_2$]PHE—NHCH$_2$Ph, and 75.3 mg (0.557 mmole) of hydroxybenzotriazole in 5 ml of DMF at 0°, was added 115 mg (0.557 mmole) of DCC. The reaction mixture was kept at 0° for one hour, then allowed to stir at room temperature for four days. The mixture was filtered, and the filtrate evaporated in vacuo at 30° to give 572 mg of crude product.

This material was taken up in CHCl$_3$ and washed with 1M citric acid, brine, saturated NaHCO$_3$, and again with brine. After drying over Na$_2$SO$_4$ and removal of the solvent under reduced pressure, there was obtained 414 mg of product.

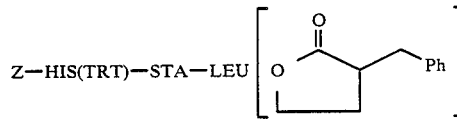

To a solution of 215 mg of BOC—STA—LEU[CHOHCH$_2$]PHE—NHCH$_2$Ph in 3 ml of CH$_2$Cl$_2$ was added 3 ml of TFA and the mixture kept at room temperature for 2.3 hours. The solvent was evaporated under reduced pressure and the residue taken up in toluene and washed several times with 1N NaOH. After drying over Na$_2$SO$_4$ and removal of the solvent under reduced pressure there was obtained 138 mg of crude material.

This was taken up in 3 ml of DMF and 189 mg of Z—HIS(TRT) and 48.4 mg of hydroxybenzotriazole added. The solution was cooled in ice and 73 mg of DCC added. After one hour at 0°, the mixture was allowed to stir at room temperature overnight. The mixture was filtered and the filtrate evaporated in vacuo. The residue was taken up in CHCl$_3$ and washed twice with saturated NaHCO$_3$ solution, then brine. Drying over Na$_2$SO$_4$ and removal of the solvent under reduced pressure gave the crude product mixture. Chromatography on silica gel, eluting with 1% MeOH in CHCl$_3$ gave 98.5 mg of high R$_f$ material,

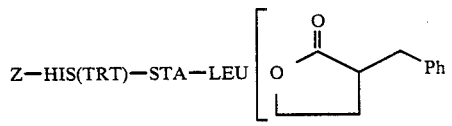

Combining fractions from lower R$_f$ material gave 62.7 mg of Z—HIS(TRT)—STA—LEU[CHOHCH$_2$]PHE—NHCH$_2$Ph.

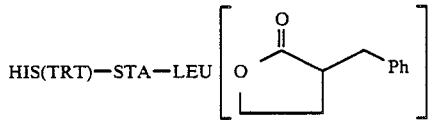

A solution of 98.5 mg of

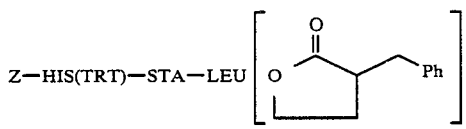

in MeOH was treated with 25 mg of 20% Pd/BaSO₄ and hydrogen was bubbled through the mixture until thin layer chromatography showed the complete removal of the Z group. The mixture was filtered through Celite and the filtrate evaporated under reduced pressure to give 89.6 mg of product.

To a cold solution of 39.5 mg (0.116 mmole) of di-(α-naphthylmethyl)acetic acid, 89.6 mg (0.112 mmole) of

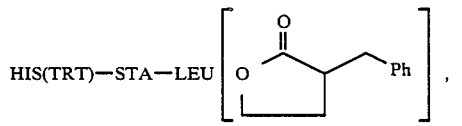

and 15.8 mg (0.117 mmole) of hydroxybenzotriazole in 2 ml of DMF was added 24.7 mg (0.118 mmole) of dicyclohexylcarbodiimide. After one hour at 0°, the mixture was allowed to stand at room temperature for two days. The mixture was filtered and the filtrate evaporated under reduced pressure. The residue was taken up in CHCl₃ and washed with 1N citric acid, brine, and saturated NaHCO₃ solution. Drying over Na₂SO₄ and removal of the solvent under reduced pressure left 180 mg of crude product. After chromatography on silica gel, eluting with 1% MeOH in CHCl₃, there was obtained 104 mg of product.

INTERMEDIATES FOR EXAMPLE 4

BOC—STA—OCH₃

BOC—STA (35.9 g, 0.13 mole), (U.S. Pat. No. 4,397,786) was dissolved in 1 l'EtOAc. An ethereal solution of diazomethane (prepared from 52 g p-tolyl-sulfonylmethylnitrosamide per *Organic Synthesis*, Collective Volume 4, pp. 251-3) was added to the EtOAc solution until a slight yellow color persisted. After stirring at 25° for two hours, glacial acetic acid was added until the yellow color disappeared. After stirring 30 minutes, the solvent was removed in vacuo giving a crystalline solid, 40.1 g. TLC, $R_f$=0.20 in 75/25 hexane/EtOAc on silica gel. The material was sufficiently pure for use in the following steps.

STA—OCH₃.HCl

BOC—STA—OCH₃ (37.4 g, 0.13 mole) was dissolved in 600 ml CH₂Cl₂ which was occasionally purged with anhydrous HCl gas over four hours. When thin layer chromatography indicated complete consumption of the starting material, the solvent was removed in vacuo and the residue resuspended in CH₂Cl₂/Et₂O which gave a crystalline solid, 30.8 g. The material was sufficiently pure for use in the following steps.

Z—STA—OCH₃

To a 1 l flask equipped with mechanical stirring was charged STA—OCH₃.HCl (29.4 g, 0.13 mole) followed by 300 ml of a 50/50 mixture of dioxane/H₂O. After cooling to 0°, benzyl chloroformate (19.6 ml, 0.137 mole) and a saturated solution of Na₂CO₃ were charged, maintaining the pH of the mixture near 11 as measured by indicator paper. After completion of the addition, the mixture was stirred for one hour at 10°, at which time pH was adjusted to 8.0 with 12% HCl solution. The dioxane was removed in vacuo, and the remaining aqueous suspension was extracted into EtOAc. The organic phase was washed with 1N citric acid solution, brine, saturated NaHCO₃ solution, brine, and dried over MgSO₄. The solution was filtered, and stripped to an oil, 40.3 g. TLC, $R_f$=0.22, in 65/35 hexane/EtOAc on silica gel. The material was sufficiently pure for use in the following steps.

PREPARATION OF

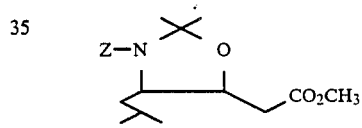

Z—STA—OCH₃ (46.3 g, 0.125 mole) was dissolved in 250 ml of 2,2-dimethoxypropane, and 30 g 4A molecular sieves was then added. After heating to 40° for one hour, 0.4 g p-toluenesulfonic acid was added, and the mixture was heated to reflux for two hours. After cooling to 25°, the mixture was filtered, and the filtrate was stripped to an oil in vacuo. The oil was suspended in saturated NaHCO₃ solution, and extracted into EtOAc. The organic phase was washed with brine, dried over MgSO₄ and filtered. The filtrate was stripped to an oil, 41.87 g. TLC, $R_f$=0.39 in 75/25 hexane/EtOAc on silica gel. The material was sufficiently pure for use in the following steps.

PREPARATION OF

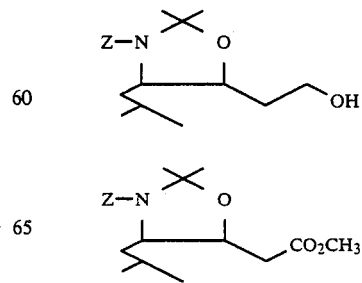

(5.0 g, 0.0138 mole) was dissolved in 80 ml dry THF, to which was added LiBH4 (0.35 g, 0.051 mole). The mixture was stirred at 25° overnight, after which 5 ml H2O was added and the solvent was removed in vacuo. The residue was suspended in EtOAc, to which was added 1N citric acid with vigorous offgassing. The organic phase was washed with brine, saturated NaHCO3, and brine, followed by drying over MgSO4, filtration, and evaporation in vacuo to an oil, 4.21 g. The oil was chromatographed on 300 g silica gel eluting with 10/90 EtOAc/hexane giving an oil, 3.49 g. Spectral and elemental analyses confirmed the proposed structure.

PREPARATION OF

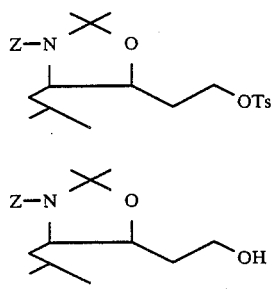

(2.55 g, 7.60 mmole) was dissolved in 30 ml CH2Cl2, to which was added Et3N (1.08 ml, 7.75 mmole) and tosyl chloride (1.48 g, 7.75 mmole). After four hours at 25°, Et3N (0.6 ml, 4.3 mmole) and tosyl chloride (0.5 g, 2.62 mmole) were added, and the mixture was stirred overnight. The solvent was removed in vacuo and the residue was taken up into EtOAc. The mixture was washed with brine, 1N citric acid, brine, saturated NaHCO3 solution, and brine. The organic phase was dried over MgSO4, filtered, and stripped to an oil, 3.98 g. The oil was chromatographed on 200 g silica gel, eluting with 15/85 EtOAc/hexane. The product was recovered as an oil, 3.02 g. Spectral and elemental analyses confirmed the proposed structure.

PREPARATION OF

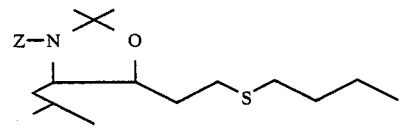

75 ml liquid NH3 was condensed into a flask which was cooled to −65°. 1-Butanethiol (2.0 ml, 0.019 mole) was added dropwise, followed by a solution of

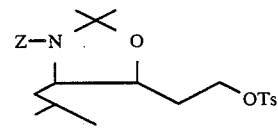

(2.74 g, 5.6 mmole) in 40 ml Et2O. The mixture was stirred overnight, allowing the NH3 to evaporate. Another 90 ml NH3 was condensed into the flask, which was allowed to evaporate over four hours. Excess butanethiol was removed in vacuo, and the residue was chromatographed on 100 g silica gel eluting with 15/85 EtOAc/hexane. The product was recovered as an oil, 1.98 g. Spectral and elemental analyses confirmed the proposed structure.

PREPARATION OF

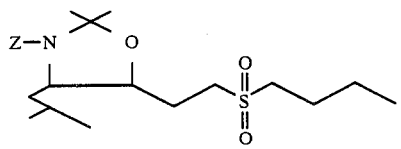

To 50 ml CH2Cl2 was added

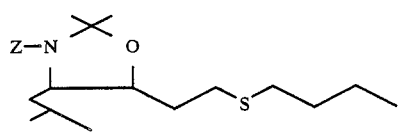

(1.84 g, 4.51 mmole) and m-chloroperoxybenzoic acid (2.35 g, 13.6 mmole) giving a mild exotherm and solution. After stirring for one hour at 25°, the solvent was removed in vacuo and the residue was dissolved in EtOAc. The mixture was washed with a solution of 20 g NaHSO3 in 100 ml H2O, followed by saturated NaHCO3 solution and brine. The organic phase was dried over MgSO4, filtered, and stripped to an oil, 2.0 g. Spectral and elemental analyses confirmed the proposed structure.

STA[CH2SO2](CH2)3CH3

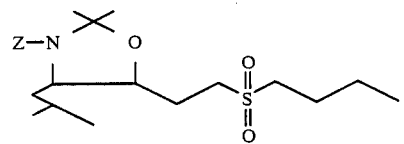

(1.66 g, 3.78 mmole) was dissolved in 75 ml MeOH, to which was added 0.17 g 20% Pd on charcoal catalyst. The mixture was purged with H2 gas for one hour, after which it was filtered and the filtrate stripped to an oil, 1.09 g. The product was sufficiently pure for use in the following steps.

Z—HIS(TRT)—STA[CH2SO29 (CH2)3CH3

To a solution of STA[CH2SO2](CH2)3CH3 (0.84 g, 3.16 mmole) in 10 ml CH2Cl2, was added a solution of Z-HIS(TRT) (1.68 g, 3.16 mmole) in 10 ml CH2Cl2, followed by a solution of hydroxybenzotriazole (0.45 g, 3.32 mmole) in 4 ml DMF. After cooling to 0°, a solution of DCC (0.69 g, 3.32 mmole) in 5 ml DMF was added, and the mixture was stirred and allowed to warm to 25° overnight. The mixture was filtered and stripped to an oil in vacuo. The residue was dissolved in EtOAc and was washed with 1N citric acid, brine, saturated NaHCO3, and brine. The organic phase was dried over MgSO4, filtered, and stripped to a foam, 2.33 g. The foam was chromatographed on 200 g silica gel eluting with a gradient of 0 to 8% MeOH in CHCl3, which gave the product as a foam, 1.60 g. This product contained a significant amount of O-acylated material at the 3-hydroxy position of the statine residue. This impurity was later hydrolyzed to the desired product following hydrogenation which is described in the following reaction.

HIS(TRT)—STA[CH$_2$SO$_2$](CH$_2$)$_3$CH$_3$

Z—HIS(TRT)—STA[CH$_2$SO$_2$](CH$_2$)$_3$CH$_3$ (1.36 g, 2.0 mmole) was dissolved in 20 ml MeOH to which 0.2 g 20% Pd on charcoal catalyst was added. The mixture was purged with H$_2$ gas for 2.5 hours, after which it was filtered and stripped to a foam, 1.04 g. The O-acylated impurity was hydrolyzed to the desired product by dissolving the foam in 50 ml MeOH, to which was added 20 drops 5N NaOH. After one hour, the MeOH was removed in vacuo, and the residue was partitioned between Et$_2$O and brine. The organic phase was dried over MgSO$_4$, filtered, and stripped to a foam, 0.60 g. Mass spectral analysis indicated a mass of 644.2; theory, 644.9. The material was sufficiently pure for use in the following step.

DNMA—HIS(TRT)—STA[CH$_2$SO$_2$](CH$_2$)$_3$CH$_3$

Di-(α-naphthylmethyl)acetic acid (0.32 g, 0.93 mmole), hydroxybenzotriazole (0.13 g, 1.0 mmole), DCC (0.21 g, 1.0 mmole) and HIS(TRT)—STA[CH$_2$SO$_2$](CH$_2$)$_3$CH$_3$ (0.60 g, 0.93 mmole) were dissolved in 18 ml CH$_2$Cl$_2$. After two hours, an additional 0.1 g DCC was added, and the mixture was stirred for four days at 25°. The mixture was then filtered and stripped to a foam, 1.09 g. The foam was dissolved in EtOAc and washed with 1N citric acid, saturated NaHCO$_3$ solution, and brine. The organic phase was dried over MgSO$_4$, filtered, and stripped to a foam, 0.90 g. The foam was chromatographed on 100 g silica gel eluting with 2% MeOH in CHCl$_3$. The product was recovered as a white foam, 0.42 g. Mass spectral analysis confirmed the structure. The material was sufficiently pure for use in the following procedure.

INTERMEDIATES FOR EXAMPLE 5

BOC—CYCLOHEXYLALA[CHOHCH$_2$](CH$_2$)$_2$CH(CH$_3$)$_2$

1-Bromo-4-methylheptane (6.77 g, 0.041 mole) and magnesium turnings (1.0 g, 0.041 g.atom) were added to 100 ml Et$_2$O. The reaction soon started. After 30 minutes an additional 0.1 ml 1-bromo-4-methoxyheptane was added and the mixture allowed to stir for one hour at 25°. In a separate flask, BOC—CYCLOHEXYLALA[CHO] (5.0 g, 0.0196 mole), U.S. Pat. No. 4,447,440, was dissolved in 200 ml Et$_2$O and cooled to −5°. The first solution thus prepared was added to the second, and the mixture was allowed to warm to 25° overnight. The mixture was washed with 1N citric acid, brine, saturated NaHCO$_3$ solution, and brine. The organic phase was dried over MgSO$_4$, filtered, and stripped to an oil, 4.81 g, which was chromatographed on 300 g silica gel eluting with 10/90 EtOAc/hexane. The product was recovered as an oil, 1.06 g. Mass spectral data indicated a molecular weight of 341.3; theory, 341.54. The material was of sufficient purity for use in the following preparations.

CYCLOHEXYLALA[CHOHCH$_2$](CH$_2$)$_2$CH(CH$_3$)$_2$.HCl

· BOC—CYCLOHEXYLALA[CHOHCH$_2$](CH$_2$)$_2$CH(CH$_3$)$_2$ (1.04 g, 3.04 mmole) was dissolved in 100 ml CH$_2$Cl$_2$ and purged with anhydrous HCl gas. After standing at 25° for 2.5 hours, the mixture was stripped to a yellow gum, 0.90 g. The material was used without further purification in the following preparations.

Z—HIS(TRT)—CYCLOHEXYLALA[CHOHCH$_2$](CH$_2$)$_2$CH(CH$_3$)$_2$

Z—HIS(TRT) (1.62 g, 3.04 mmole) and hydroxybenzotriazole (0.43 g, 3.19 mmole) were dissolved in 35 ml DMF and cooled to −5°. To this mixture was added a solution prepared from CYCLOHEXYLALA[CHOHCH$_2$](CH$_2$)$_2$CH(CH$_3$)$_2$.HCl (0.85 g, 3.04 mmole) and Et$_3$N (0.44 ml, 3.19 mmole) in 20 ml cold DMF. To this mixture was charged a solution of DCC (0.66 g, 3.19 mmole) in several mls of cold DMF. While stirring overnight, the mixture was allowed to warm to 25°, after which it was filtered and stripped in vacuo to an oil. The residue was taken up into EtOAC and washed with 1N citric acid, brine, saturated NaHCO$_3$ solution, and brine. The organic phase was dried over MgSO$_4$, filtered, and stripped to a yellow foam, 2.37 g, which was chromatographed on 100 g silica gel, eluting with EtOAc. The product was recovered as a foam, 1.94 g, and was of suitable purity for use in the following preparations.

HIS(TRT)—CYCLOHEXYLALA[CHOHCH$_2$](CH$_2$)$_2$CH(CH$_3$)$_2$

Z—HIS(TRT)—CYCLOHEXYLALA[CHOHCH$_2$](CH$_2$)$_2$CH(CH$_3$)$_2$ (1.94 g, 2.57 mmole) was dissolved in 100 ml MeOH to which 0.24 g 20% Pd on charcoal catalyst was added. The mixture was purged with H$_2$ gas for 2.5 hours, after which it was filtered and stripped to a glass, 1.50 g. The material was sufficiently pure for use in the following step.

DNMA—HIS(TRT)—CYCLOHEXYLALA[CHOHCH$_2$](CH$_2$)$_2$CH(CH$_3$)$_2$

Di-(α-naphthylmethyl)acetic acid (0.82 g, 2.42 mmole), hydroxybenzotriazole (0.343 g, 2.54 mmole), DCC (0.523 g, 2.54 mmole) and HIS(TRT)—CYCLOHEXYLALA[CHOHCH$_2$](CH$_2$)$_2$CH(CH$_3$)$_2$ (1.50 g, 2.42 mmole) were dissolved in 40 ml DMF and cooled to −5° for several hours. After being stored at 4° for 48 hours, the mixture was filtered, stripped to an oil in vacuo, and the residue dissolved in EtOAc. The solution was washed with 1N citric acid, brine, saturated NaHCO$_3$ solution, and brine. The organic phase was dried over MgSO$_4$, filtered, and stripped to a yellow foam, 2.59 g, which was chromatographed on 200 g silica gel eluting with 25/75 hexane/EtOAc. The product was recovered as a foam, 1.88 g, of sufficient purity for use in the following preparation.

INTERMEDIATES FOR EXAMPLE 6

BOC—CYCLOHEXYLALA[CHOHCH$_2$](CH$_2$)$_5$CH$_3$ n-Heptylbromide (7.34 g, 0.041 mole) and magnesium turnings (1.0 g, 0.041 g.atom) were added to 100 ml Et$_2$O. The reaction soon started. After 30 minutes an additional 0.1 ml N-heptylbromide was added and the mixture was allowed to stir for one hour at 25°. In a separate flask, BOC—CYCLOHEXYLALA[CHO] (5.0 g, 0.0196 mole), U.S. Pat. No. 4,477,440, was dissolved in 200 ml Et$_2$O and cooled to −5°. The first solution thus prepared was added to the second, and the mixture was allowed to warm to 25° overnight. The mixture was washed with 1N citric acid, brine, saturated NaHCO$_3$ solution, and brine. The organic phase was dried over MgSO$_4$, filtered, and stripped to an oil, 5.89 g, which was chromatographed on 300 g silica gel eluting with 10/90 EtOAc/hexane. The product was recovered as an oil, 2.88 g. Mass spectral data indicated a molecular weight of 355.2; theory, 355.56. The material was of suitable purity for use in the following preparation.

CYCLOHEXYLALA[CHOHCH$_2$](CH$_2$)$_5$CH$_3$·HCl

BOC—CYCLOHEXYLALA[CHOHCH$_2$](CH$_2$)$_5$CH$_3$ (2.88 g, 8.10 mmole) was dissolved in 100 ml CH$_2$Cl$_2$ and purged with anhydrous HCl gas. After standing at 25° for 2.5 hours, the mixture was stripped to a yellow gum, 2.14 g. The material was used without further purification in the following preparation.

Z—HIS(TRT)—CYCLOHEXYLALA[CHOHCH$_2$](CH$_2$)$_5$CH$_3$

Z—HIS(TRT) (3.9 g, 7.33 mmole) and hydroxybenzotriazole (1.04 g, 7.70 mmole) were dissolved in 75 ml DMF and cooled to −5°. To this mixture was added a solution prepared from CYCLOHEXYLALA[CHOHCH$_2$](CH$_2$)$_5$CH$_3$·HCl (2.14 g, 7.33 mmole) and Et$_3$N (1.07 ml, 7.70 mmole) in 35 ml DMF. To this mixture was charged a solution of DCC (1.59 g, 7.70 mmole) in several mls of cold DMF. While stirring overnight, the mixture was allowed to warm to 25°, after which it was filtered and stripped in vacuo to an oil. The residue was taken up into EtOAc and washed with 1N citric acid, brine, saturated NaHCO$_3$ solution, and brine. The organic phase was dried over MgSO$_4$, filtered, and stripped to a yellow foam, 5.87 g, which was chromatographed on 200 g silica gel, eluting with EtOAc. The product was recovered as a foam, 4.84 g, and was of suitable purity for use in the following preparations.

HIS(TRT)—CYCLOHEXYLALA[CHOHCH$_2$](CH$_2$)$_5$CH$_3$

Z—HIS(TRT)—CYCLOHEXYLALA[CHOHCH$_2$](CH$_2$)$_5$CH$_3$ (4.84 g, 6.29 mmole) was dissolved in 150 ml MeOH to which 0.32 g 20% Pd on charcoal catalyst was added. The mixture was purged with H$_2$ gas for 2.5 hours, after which it was filtered and stripped to a glass, 3.79 g. The material was sufficiently pure for use in the following step.

DMA—HIS(TRT)—CYCLOHEXYLALA[CHOHCH$_2$](CH$_2$)$_5$CH$_3$

Di-(α-naphthylmethyl)acetic acid (1.01 g, 2.98 mmole), hydroxybenzotriazole (0.422 g, 3.12 mmole), DCC (0.644 g, 3.12 mmole) and HIS(TRT)—CYCLOHEXYLALA[CHOHCH$_2$](CH$_2$)$_5$CH$_3$ (1.90 g, 2.98 mmole) were dissolved in 40 ml DMF and cooled to −5° for several hours. After being stored at 4° for 48 hours, the mixture was filtered, stripped to an oil in vacuo, and the residue dissolved in EtOAc. The solution was washed with 1N citric acid, brine, saturated NaHCO$_3$ solution, and brine. The organic phase was dried over MgSO$_4$, filtered, and stripped to a yellow foam, 2.98 g, which was chromatographed on 200 g silica gel eluting with 50/50 hexane/EtOAc. The product was recovered as a foam, 2.38 g, of sufficient purity for use in the following preparation.

INTERMEDIATES FOR EXAMPLE 7

PREPARATION OF

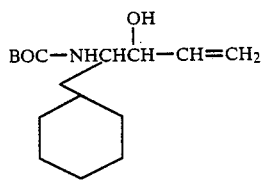

BOC—CYCLOHEXYLALA[CHO] (4.74 g, 0.186 mole), U.S. Pat. No. 4,447,440, was dissolved in 200 ml Et$_2$O and cooled to −5°. 37 ml vinyl magnesium bromide (1.0–1.5M in THF) was added dropwise over 10 minutes. The mixture was allowed to warm to 25° overnight. The mixture was washed with 1N citric acid, saturated NaHCO$_3$ solution, and brine. The organic phase was dried over MgSO$_4$, filtered, and stripped to an oil, 5.62 g. The oil was chromatographed on 300 g silica gel eluting with 10/90 EtOAc/hexane. The product was recovered as an oil, 1.85 g, which was sufficiently pure for use in the following procedures.

PREPARATION OF

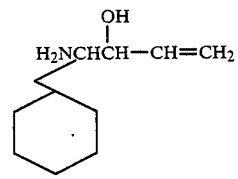

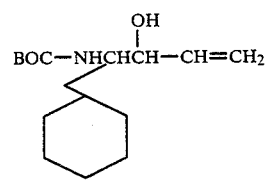

(1.81 g, 6.38 mmole) was dissolved in a solution of 25 ml CH$_2$Cl$_2$ and 10 ml TFA and stirred at 25° for one hour. The solvent was removed in vacuo and the residue taken up in EtOAc. This was washed with brine which had been adjusted to pH 10 with 1N NaOH, then with brine. After drying over MgSO$_4$, removal of the solvent under reduced pressure left 1.26 g of a brown oil. The material was of sufficient purity for use in the following steps.

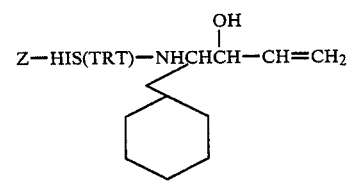

Z—HIS(TRT) (3.39 g, 6.38 mmole), hydroxybenzotriazole (0.91 g, 6.70 mmole) and

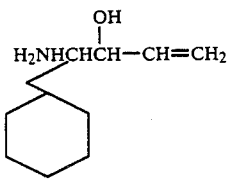

(1.17 g, 6.38 mmole) were dissolved in 40 ml DMF and cooled to −5°. A solution of DCC (1.38 g, 6.70 mmole) in 10.0 ml cold DMF was added, and the mixture was stored at 4° for 48 hours. The mixture was filtered and the solvent was removed in vacuo. The residue was taken up into EtOAc, washed with 1N citric acid, brine, saturated NaHCO$_3$ solution, and brine. The organic phase was dried over MgSO$_4$, filtered, and stripped to a foam, 4.82 g. The oil was chromatographed on 300 g silica gel, eluting with 50/50 hexane/EtOAc, to give the O,N-diacylated product as a foam, 1.40 g, and the desired product as a foam, 2.34 g. The diacylated product was hydrolyzed to the desired product as follows.

1.40 g of diacylated product was dissolved in 20 ml MeOH to which 0.5 g NaOH was added. After three hours stirring at 25°, the pH was adjusted to 7.0 with 12% HCl, and the mixture was stored at 25° overnight. The mixture was stripped and the residue was taken up into EtOAc. The solution was washed with 1N citric acid, brine, saturated NaHCO$_3$ solution, and brine. The organic phase was dried over MgSO$_4$, filtered, and stripped to a foam, 1.19 g. This was combined with the 2.34 g of desired product obtained above, for a total of 3.53 g, usable without further purification in the following preparations.

Z—HIS(TRT)—CYCLOHEXYLALA[CHOH-CHOH]CH$_2$OH

To a solution of

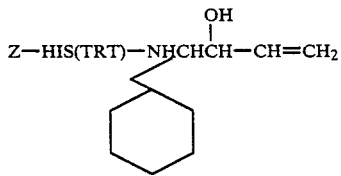

(3.4 g, 4.88 mmole) in 40 ml of dioxane was added 37 ml of a 0.157N solution of osmic acid in dioxane, and the solution stirred at 25° for four days. The mixture was purged with H$_2$S gas for two hours, then filtered through Celite. The filtrate was stripped to a black oil, 4.94 g, which was chromatographed on 300 g silica gel eluting with 5/95 MeOH/CHCl$_3$. The product was recovered as a brown-black foam, 1.64 g, of sufficient purity for use in the following

HIS(TRT)—CYCLOHEXYLALA[CHOHCHOH]C-H$_2$OH

Z—HIS(TRT)—CYCLOHEXYLALA[CHOH-CHOH]CH$_2$OH (1.64 g, 2.24 mmole) was dissolved in 30 ml MeOH which contained 0.16 g 20% Pd on charcoal catalyst. The mixture was purged with H$_2$ gas for three hours, filtered, and stripped to a black foam, 1.25 g, of sufficient purity for use in the following procedures.

DNMA—HIS(TRT)—CYCLOHEXYLALA[CHOH-CHOH]CH$_2$OH

Di-(α-naphthylmethyl)acetic acid (0.76 g, 2.24 mmole), hydroxybenzotriazole (0.32 g, 2.35 mmole) and HIS(TRT)—CYCLOHEXYLALA[CHOHCHOH]C-H$_2$OH (1.25 g, 2.09 mmole) were dissolved in 30 ml DMF and cooled to 5°. DCC (0.48 g, 2.35 mmole) was added, and the mixture was stored at 4° for three days. The mixture was filtered, stripped in vacuo, and the residue resuspended in EtOAc. The solution was washed with 1N citric acid, brine, saturated NaHCO$_3$ solution, and brine. The organic phase was dried over MgSO$_4$, filtered, and stripped to a black foam, 2.0 g. The foam was chromatographed on 100 g silica gel, eluting with 5/95 MeOH/CHCl$_3$, giving a grey solid, 0.81 g, of sufficient purity to be used in the following procedure.

INTERMEDIATES FOR EXAMPLE 8

Z—HIS(TRT)—N(CH$_3$)OCH$_3$

Z—HIS(TRT) (19.3 g) was dissolved in dichloromethane (300 ml) and cooled to 0°. Carbonyldiimidazole (5.1 g) was added and the mixture was stirred for three hours. A suspension of O,N-dimethylhydroxyamine hydrochloride (3.55 g) and triethylamine (5 ml) in dichloromethane (70 ml) was added to the mixture and the resulting suspension warmed to 25° and stirred overnight. The mixture was extracted with water, citric acid, sodium bicarbonate, and brine. The extract was dried over sodium sulfate, filtered, and evaporated. The residue was recrystallized from ethyl acetate, mp 153°–155°, 20 g.

Z—HIS(TRT)[CHO]

Z—HIS(TRT)—N(CH$_3$)OCH$_3$ (2.0 g) was dissolved in tetrahydrofuran and cooled to 0°. Lithium aluminum hydride (0.25 g) was added and the mixture stirred for 30 minutes. Acetone (1 ml) and citric acid (1N) (20 ml) were added and the mixture extracted with ethyl acetate. The organic phase was washed with citric acid, sodium bicarbonate, and brine. The extract was dried over sodium sulfate, filtered, and evaporated to give the aldehyde (1.6 g).

BOC—STA—NHCH$_2$CH(CH$_3$)CH$_2$CH$_3$

BOC—STA (27.53 g, 0.1 mole), (U.S. Pat. No. 4,397,786) and hydroxybenzotriazole (14.2 g, 0.105 mole) were dissolved in 40 ml DMF. 300 ml CH$_2$Cl$_2$ was added, and the mixture was cooled to 0°. A solution of DCC (21.66 g, 0.105 mole) in 50 ml CH$_2$Cl$_2$ was added, followed by S-2-methylbutylamine (12 ml, 0.1 mole). After stirring at 0° for two hours, the mixture was allowed to warm to 25° over 1.5 hours. The mixture was filtered and the solvent was removed in vacuo. The residue was dissolved in EtOAc, which was washed with 1N citric acid, brine, saturated NaHCO$_3$ solution, and brine. The organic phase was dried over MgSO$_4$, filtered, and stripped to a gum, 36.90 g. The gum was dissolved in Et$_2$O and treated with charcoal to remove colored impurities. Filtering and removal of the solvent under reduced pressure gave 35.2 g of a gum which was sufficiently pure for use in subsequent reactions.

STA—NHCH$_2$CH(CH$_3$)CH$_2$CH$_3$.HCl

BOC—STA—NHCH$_2$CH(CH$_3$)CH$_2$CH$_3$ (34.4 g, 0.1 mole) was dissolved in 250 CH$_2$Cl$_2$ and the solution was purged occasionally with anhydrous HCl gas over three hours. A solid precipitated from solution which was filtered, washed with CH₂Cl₂, and dried at 40° in vacuo to a hygroscopic solid, 21 g. The solid was triturated with a mixture of CH₂Cl₂/Et₂O, filtered, and dried at 40° in vacuo to a white solid, 19.34 g. Spectral and elemental analysis confirmed the structure.

Z—HIS(TRT)[CH₂NH]-STA—NHCH₂CH(CH₃)CH₂CH₃

STA—NHCH₂CH(CH₃)CH₂CH₃·HCl (4.21 g, 0.015 mole) was suspended in EtOAc and washed with saturated NaHCO₃ solution. The organic phase was dried over MgSO₄, filtered, and stripped to an oil, which was resuspended in 100 ml dry EtOH. To this solution was added Z—HIS(TRT)[CHO] (7.5 g, 0.145 mole) followed by 36.5 g 3A molecular sieves. The mixture was stirred at 25° overnight, after which NaCNBH₃ (0.88 g, 0.014 mole) was added. This was followed by the addition of three portions of citric acid (0.88 g) at two hour intervals, after which the mixture was stirred overnight at 25°. The mixture was filtered, the solvent removed in vacuo, and the residue taken up into EtOAc/1N citric acid. The pH of the mixture was adjusted to 9.0 with 5N NaOH, and the organic phase separated and dried over MgSO₄. Removal of the solvent under reduced pressure gave a foam, which was chromatographed on 500 g silica gel, eluting with a gradient of 0 to 10% MeOH in CHCl₃. The product was recovered as a foam, 6.0 g, which was sufficiently pure for use in the following steps.

Z—HIS(TRT)[CH₂N(BOC)]-STA—NHCH₂CH(CH₂CH₃

Z—HIS(TRT)[CH₂NH]-STA—NHCH₂CH(CH₃)CH₂CH₃ (6.0 g, 8.06 mmole) and di-t-butyl-di-carbonate (1.84 g, 8.46 mmole) were dissolved in 150 ml CH₂Cl₂ and stripped overnight at 25°. Et₃N (0.6 ml, 4.31 mmole) and di-t-butyl-di-carbonate (0.68 g, 3.12 mmole) were then added, and the mixture was refrigerated overnight. The mixture was then stripped of solvent and the residue was resuspended in EtOAc. The suspension was washed with 1N citric acid, brine, saturated NaHCO₃ solution, and brine. The organic phase was dried over MgSO₄, filtered, and stripped to an oil, 6.7 g. The oil was chromatographed on 300 g silica gel, eluting with a gradient of 0 to 2% MeOH in CHCl₃. The product was recovered as a white foam, 4.12 g, which was sufficiently pure for use in the following steps.

HIS(TRT)]CH₂N(BOC)]-STA—NHCH₂CH(CH₃)CH₂CH₃

Z—HIS(TRT)[CH₂N(BOC)]-STA—NHCH₂CH(CH₃)CH₂CH₃ (4.0 g, 4.74 mmole) was dissolved in 75 ml MeOH, to which was added 0.3 g 20% Pd on charcoal catalyst. The mixture was purged with H₂ gas for two hours, filtered, and stripped to a white foam, 3.35 g, which was sufficiently pure for use in the following steps.

DMA—HIS(TRT)[CH₂N(BOC)]-STA—NHCH₂CH(CH₃)CH₂CH₃

Di-(α-naphthylmethyl)acetic acid (0.82 g, 2.41 mmole) hydroxybenzotriazole (0.342 g, 2.53 mmole), DCC (0.52 g, 2.53 mmole), and HIS(TRT)[CH₂N(BOC)]STA-NHCH₂CH(CH₃)CH₂CH₃ (1.71 g, 2.41 mmole) were dissolved in 25 ml DMF and stirred at 25° overnight. The mixture was filtered, stripped in vacuo to an oil, and the residue was taken up into EtOAC. The suspension was washed with 1N citric acid, brine, saturated NaHCO₃ solution, and brine. The organic phase was dried over MgSO₄, filtered, and stripped to a foam, 2.83 g. The foam was chromatographed on 200 g silica gel, eluting with a gradient of 0 to 5% MeOH in EtOAc. The product was recovered as a white foam, 2.16 g. The material was used without further purification in the following step.

INTERMEDIATES FOR EXAMPLES 9 AND 10

PREPARATION OF

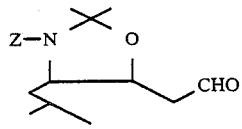

A solution of 12.13 g (0.033 mole) of

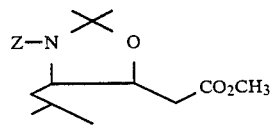

in 350 ml toluene was cooled to −68°. A solution of diisobutylaluminum hydride (1.5M in toluene) was added over three minutes, with an exotherm to −55°. After stirring for 45 minutes at −55°, the mixture was cooled to −65°. 150 ml cold 2N HCl was added with an exotherm to −2°. After warming to 0°, the mixture was filtered, and the organic phase was washed with 1N citric acid, brine, saturated NaHCO₃, and brine. The organic phase was dried over MgSO₄, filtered, and stripped in vacuo to an oil, 11.33 g. The crude product was chromatographed on 300 g silica gel, eluting with a gradient of 90/10 hexane/EtOAc to 80/20 hexane/EtOAc. A clear oil was recovered, 9.6 g. The structure was confirmed by spectral and elemental analyses.

PREPARATION OF

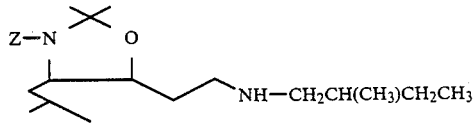

25 g of activated 3A molecular sieves were added to a solution of S-2-methylbutylamine (5.0 ml, 0.043 mole) in 50 ml dry THF. A solution of

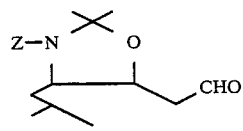

(8.75 g, 0.026 mole) in 40 ml dry THF was added, and the mixture was stirred overnight. The mixture was acidified with a solution of anhydrous HCl gas in THF until indicator paper indicated the pH to be 5.5–6.0. NaCNBH$_3$ (1.97 g, 0.0313 mole) was added and the mixture stirred overnight. The mixture was filtered and stripped in vacuo to an oil, 13.7 g.

The mixture was chromatographed on 800 g silica gel, eluting with a 50/49/1 ratio of CHCl$_3$/EtOAc/MeOH. The product was recovered as an oil, 4.88 g. The structure was confirmed by spectral and elemental analyses. The mixture was sufficiently pure for use in the following reaction.

Z—STA[CH$_2$NH]CH$_2$CH(CH$_3$)CH$_2$CH$_3$

To 45 ml of a solution consisting of equal amounts of TFA, MeOH, and CHCl$_3$ was added

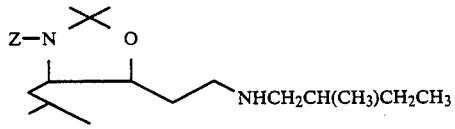

(4.3 g, 10.63 mmole) and the solution stirred at room temperature for 45 minutes. The mixture was stripped to an oil, additional solvent added, and the mixture stripped again. The resulting oil was suspended in H$_2$O and the pH brought to 13 with 5N NaOH. The oil was extracted with Et$_2$O, washed with brine, and dried over MgSO$_4$. Removal of the solvent under reduced pressure left 3.89 g of an oil. Spectral and elemental analyses confirmed the structure.

Z—STA[CH$_2$N(BOC)]CH$_2$CH(CH$_3$)CH$_2$CH$_3$

Z—STA[CH$_2$NH]CH$_2$CH(CH$_3$)CH$_2$CH$_3$ (3.73 g, 10.23 mmole) was dissolved in 100 ml MeOH to which was added di-t-butyldicarbonate (2.4 g, 11.3 mmole). After stirring overnight the mixture was stripped to an oil and chromatographed on 300 g silica gel, eluting with a gradient of 15/85 EtOAc/hexane to 25/75 EtOAc/hexane. The product was recovered as an oil, 4.35 g. Spectral and elemental analyses confirmed the structure.

STA[CH$_2$N(BOC)]CH$_2$CH(CH$_3$)CH$_2$CH$_3$

To a solution of Z—STA[CH$_2$N(BOC)]CH$_2$CH(CH$_3$)CH$_2$CH$_3$ (3.87 g, 8.33 mmole) in 100 ml MeOH was added 0.12 g of 20% Pd on charcoal catalyst, followed by purging with H$_2$ gas. After two hours, the mixture was filtered and stripped to a clear oil, 2.70 g. Spectral and elemental analyses confirmed the structure.

Z—HIS(TRT)—STA[CH$_2$N(BOC)]CH$_2$CH(CH$_3$)CH$_2$CH$_3$

Z—HIS(TRT), (4.0 g, 7.35 mmole) and hydroxybenzotriazole (1.04 g, 7.72 mmole) were dissolved in 6 ml DMF. The mixture was cooled to −5°, and 50 ml CH$_2$Cl$_2$ was added. A cold solution of DCC (1.59 g, 7.72 mmole) in 10 ml CH$_2$Cl$_2$ was added, followed by a cold solution of STA[CH$_2$N(BOC)CH$_2$-CH—(CH$_3$CH$_2$CH$_2$ (2.43 g, 7.35 mmole) in 20 ml CH$_2$Cl$_2$. The mixture was stirred and allowed to warm to 25° overnight. The mixture was filtered, and the filtrate substrate to an oil. The oil was dissolved in EtOAc, filtered, and washed with brine, 1N citric acid, brine, saturated NaHCO$_3$ solution, and brine. The organic phase was dried over MgSO$_4$, filtered, and stripped to a foam. The foam was suspended in Et$_2$O, filtered, and the filtrate stripped to a foam, 6.35 g. The material was chromatographed on 500 g silica gel, eluting with 5/95 MeOH/CHCl$_3$. The product was recovered as a white foam, 5.81 g. Spectral and elemental analyses confirm the structure.

HIS(TRT)—STA—CH$_2$N(BOC)]CH$_2$CH(CH$_3$)CH$_2$CH$_3$

To a solution of Z—HIS(TRT)—STA[CH$_2$N(BOC)]CH$_2$CH(CH$_3$)CH$_2$CH$_3$ (4.96 g, 5.88 mmole) in 200 ml MeOH was charged 0.20 g of 20% Pd on charcoal catalyst. The mixture was purged with H$_2$ gas for several hours. An additional 0.20 g catalyst was charged, and the reaction was allowed to proceed overnight. The mixture was filtered, stripped to a foam, and chromatographed on 200 g silica gel, eluting with 5/95 MeOH/CHCl$_3$. The product was recovered as a white foam, 3.77 g. Spectral and elemental analyses confirmed the structure.

DNMA—HIS(TRT)—STA[CH$_2$N(BOC)]CH$_2$CH(CH$_3$)CH$_2$CH$_3$

Di-(α-naphthylmethyl)acetic acid (1.02 g, 3.0 mmole) and hydroxybenzotriazole (0.43 g, 3.15 mmole) were dissolved in 4 ml DMF. 20 ml CH$_2$Cl$_2$ was added, and the mixture was cooled to 0°. A solution of DCC (0.65 g, 3.15 mmole) in 10 ml cold CH$_2$Cl$_2$ was added, followed by a solution of HIS(TRT)—STA[CH$_2$N(BOC)CH$_2$CH(CH$_3$)CH$_2$CH$_3$ (2.13 g, 3.0 mmole) in 20 ml CH$_2$Cl$_2$. The mixture was stirred and allowed to warm to 25° overnight. The mixture was filtered, and stripped to an oil which was resuspended in EtOAc. The solution was washed with brine and 1N citric acid, followed by filtration. The filtrate was washed with brine, saturated NaHCO$_3$ solution, and brine. The solution was dried over MgSO$_4$, filtered, and stripped to a foam, 3.40 g. The foam was chromatographed on 200 g silica gel eluting with CHCl$_3$ to give another foam. This was taken up in Et$_2$O, filtered, and stripped to a foam, 2.76 g. Spectral and elemental analyses confirmed the structure.

INTERMEDIATES FOR EXAMPLE 11

BOC—CYCLOHEXYLALA

BOC—PHE (40 g) was dissolved in isopropanol. (400 ml) and 20% Rh/C (4.0 g) was added. The system was pressurized to 50 psi and shaken until the theoretical amount of hydrogen was taken up. The system was then flushed with nitrogen and filtered. The solvent was evaporated and the residue mixed with dichloromethane and evaporated to give 46 g of product.

Calcd. for C$_{14}$H$_{25}$NO$_4$·0.143CH$_2$Cl$_2$: C, 59.52; H, 8.99; N, 4.94. Found: C, 60.17; H, 9.04; N, 4.71.

BOC—CYCLOHEXYLALA[COCHN$_2$]

BOC—CYCLOHEXYLALA (20 g) was dissolved in ethyl acetate (200 ml) and cooled to −20°. N-methyl piperidine (8.5 ml) was added, followed by a dropwise addition of isobutyl chloroformate (9.56 ml). The mixture was stirred for 10 minutes and then filtered under nitrogen into a cold flask. Diazomethane (8 g) in ether was added and the mixture allowed to stand at 2° overnight. Nitrogen was bubbled through the solution to remove any excess diazomethane. The solvent was washed with water, sodium bicarbonate, and brine. The organic phase was dried over sodium sulfate, filtered, and evaporated. The residue was recrystallized from hexane to give 13 g of product, mp 93°–94°.

Analysis: Calcd. C, 60.99; H, 8.52; N, 14.23. Found: C, 61.02; H, 8.75; N, 14.10.

$[\alpha]_D^{23} = -60.8°$ (C, 1.10, EtOH).

BOC—CYCLOHEXYLALA[COCH$_2$Br]

BOC—CYCLOHEXYLALA[COCHN$_2$] (10 g) was dissolved in ether (300 ml) and cooled to −20°. Gaseous hydrogen bromide was bubbled into the ether solution until the pH measured 1. The mixture was washed with 1N citric acid, sodium bicarbonate, and brine. The organic layer was dried over sodium sulfate, filtered, and evaporated. The residue was recrystallized from hexane to give 10.2 g of product, mp 89°–90°.

Analysis: Calcd. C, 51.73; H, 7.52; N, 4.02. Found: C, 52.03; H, 7.51; N, 3.87.

$[\alpha]_D^{23} = -61.6°$ (C, 1.29, EtOH).

BOC—CYCLOHEXYLALA[COCH$_2$CH(CO$_2$CH$_2$Ph)$_2$]

Sodium hydride (0.83 g) (60%) was washed with hexane and then suspended in THF (30 ml). Dibenzyl malonate (5 g) in THF (40 ml) was added slowly. The mixture was stirred for one hour at 25° and then cooled to 0°. BOC—CYCLOHEXYLALA[COCH$_2$Br] (6 g) in THF (20 ml) was added. The mixture was stirred for 0.5 hours at 0°, then warmed to 25° and stirred for one nol (20 ml) and cooled to 0°. Sodium borohydried (0.8 g) and ether. The organic layer was washed with sodium bicarbonate and brine. The extract was dried over sodium sulfate, filtered and evaporated. The residue was eluted from silica gel with 25° ether/hexane to give 9 g of product.

Analysis: Calcd. C, 69.07; H, 7.49; N, 27.57. Found: C, 69.73; H, 7.61; N, 2.62.

BOC—CYCLOHEXYLALA[COCH$_2$]GLY

BOC—CYCLOHEXYLALA[COCH$_2$CH(CO$_2$CH$_2$Ph)$_2$] (3 g) was dissolved in methanol (15 ml). Palladium on carbon (0.3 g) was added and the flask flushed with hydrogen. The mixture was stirred for two hours and then flushed with nitrogen. The mixture was filtered and the solvent evaporated. The residue was dissolved in toluene and heated to reflux for four hours. The mixture was cooled and the solvent evaporated to give 1.9 g of product.

BOC—CYCLOHEXYLALA[COCH$_2$]-GLY—LEU—NHCH$_2$Ph

BOC—CYCLOHEXYLALA[COCH$_2$]GLY (0.8 g), LEU—NHCH$_2$Ph.HCl (0.52 g), triethylamine (0.28 ml), and hydroxybenzotriazole (0.27 g) were stirred together in dimethylformamide (20 ml). The mixture was cooled to 0° and dicyclohexylcarbodiimide (0.41 g) added. The mixture was allowed to warm slowly to 25° and stir for 24 hours. The mixture was filtered and the filtrate extracted with ethyl acetate and water. The organic layer was washed with water, sodium bicarbonate, and brine. The extract was dried over sodium sulfate, filtered, and evaporated. The residue was eluted from silica gel with 4:1 hexane/ethyl acetate to give 0.9 g of product.

BOC—CYCLOHEXYLALA[CHOHCH$_2$]-GLY—LEU—NHCH$_2$Ph

BOC—CYCLOHEXYLALA[COCH$_2$]-GLY—LEU—NHCH$_2$Ph (0.9 g) was dissolved in ethanol (20 ml) and cooled to 0°. Sodium borohydride (0.8 g) was added and the mixture was allowed to warm to 25° stir for two hours. Acetic acid and water 1:1 was added and the solvent evaporated. The residue was extracted with ethyl acetate and sodium bicarbonate. The organic layer was washed with brine, dried over sodium sulfate, filtered, and evaporated to give 0.8 g of product.

CYCLOHEXYLALA[CHOHCH$_2$]-GLY—LEU—NHCH$_2$Ph

BOC—CYCLOHEXYLALA[CHOHCH$_2$]-GLY—LEU—NHCH$_2$Ph (0.8 g) was dissolved in dichloromethane (20 ml) and trifluoroacetic acid (2 ml) was added. The mixture was stirred at 25° for two hours. The solvent was evaporated and the residue extracted with ethyl acetate and sodium carbonate. The organic layer was washed with brine, dried over sodium sulfate, filtered, and evaporated to give 0.6 g of product.

Z—HIS(TRT)—CYCLOHEXYLALA[CHOHCH$_2$]-GLY—LEU—NHCH$_2$Ph

CYCLOHEXYLALA[CHOHCH$_2$]-GLY—LEU—NHCH$_2$Ph (0.8 g), Z—HIS(TRT) (1.6 g), and hydroxybenzotriazole (0.27 g) were stirred together in dimethylformamide (15 ml) and cooled to 0°. Dicyclohexylcarodiimide (0.41 g) was added and the mixture allowed to warm slowly to 25° and stir for 24 hours. The mixture was filtered and the filtrate extracted with ethyl acetate and water. The organic phase was washed with water, sodium bicarbonate, and brine. The extract was dried over sodium sulfate, filtered, and evaporated. The residue was eluted from silica gel with ethyl acetate to give 0.5 g of the desired product.

HIS(TRT)—CYCLOHEXYLALA[CHOCH$_2$]-GLY—LEU—NHCH$_2$Ph

Z—HIS(TRT)—CYCLOHEXYLALA[CHOCH$_2$]-GLY—LEU—NHCH$_2$Ph (0.5 g) was dissolved in methanol (15 ml) and palladium on carbon (20%) 0.1 g was added. The flask was flushed with hydrogen and the mixture stirred for three hours. The flask was flushed with nitrogen and the mixture filtered. The solvent was evaporated to give 0.4 g of product.

DNMA—HIS(TRT)—CYCLOHEXYLALA[CHOHCH$_2$]GLY—LEU—NHCH$_2$Ph

HIS(TRT)—CYCLOH EXYLALA[CHOHCH$_2$]-GLY—LEU—NHCH$_2$Ph (0.5 g), di-($\alpha$-naphthylmethyl)acetic acid, (0.21 g), and hydroxybenzotriazole (0.1 g) were dissolved in DMF (10 ml) and cooled to 0°. Dicyclohexylcarbodiimide (0.13 g) was added and the mixture was allowed to warm slowly to 25°. The mixture was stirred for 24 hours and then filtered. The filtrate was extracted with ethyl acetate and water. The organic layer was washed with water, sodium bicarbonate, and brine. The extract was dried over sodium sulfate, filtered, and evaporated. The residue was eluted from silica gel with 1:1 ethyl acetate/hexane then 3:1 ethyl acetate/hexane to give 0.4 g of product.

INTERMEDIATES FOR EXAMPLE 12

Z—CYCLOHEXYLALA

PHE (100 g) was dissolved in water (1 l) with sodium hydroxide (25 g). Rhodium on carbon (10%) (15 g) was added and the mixture was flushed with hydrogen. The system was pressurized to 50 psi for two hours. The mixture was filtered and the filtrate was cooled to 0°.

Dioxane (300 ml) was added and a simultaneous addition of 25 g of sodium hydroxide in 250 ml of water and benzyl chloroformate (100 g) was started. The mixture was stirred for one hour after the addition was complete. The mixture was extracted with ether and the aqueous phase was acidified with concentrated HCl to pH 1. The mixture was extracted with ether and the organic layer was washed with water and brine. The extract was dried over sodium sulfate, filtered, and evaporated to give 170 g of product.

Z—CYCLOHEXYLALA[COCHN$_2$]

Z—CYCLOHEXYLALA (30g) was dissolved in ethyl acetate (250 ml) and cooled to −20°. N-methyl piperidine (12 ml) was added followed by a dropwise addition of isobutyl chloroformate (13 ml). The mixture was stirred for ten minutes and then filtered under nitrogen into a cold flask. Diazomethane (8 g) in ether was added and the mixture was allowed to stand at 0° overnight. Nitrogen was bubbled through the solution to remove any excess diazomethane. The solvent was washed with water, sodium bicarbonate, and brine. The organic phase was dried over sodium sulfate, filtered, and evaporated to give 31.7 g of product.

Z—CYCLOHEXYLALA[COCH$_2$Br]

Z—CYCLOHEXYLALA[COCHN$_2$] (31.7 g) was dissolved in ether (200 ml) and cooled to −20°. Hydrogen bromide gas was bubbled into the solution until the nitrogen evolution stopped. The solution had a pH of 1. The mixture was extracted with sodium bicarbonate and brine. The organic layer was dried over sodium sulfate, filtered, and evaporated. The residue was recrystallized from hexane to give 21.5 g of product, mp 63°-64°.

Calcd. for C$_{18}$H$_{24}$NO$_3$Br: C, 56.55; H, 6.33; N, 3.66. Found: C, 56.97; H, 6.25; N, 3.99.

Z—CYCLOHEXYLALA[COCH$_2$CH(CO$_2$—t—Bu)$_2$]

Sodium hydride (1.41 g) (50% in mineral oil) was washed with hexane and then suspended in DMF (100 ml). Di-tert-butyl malonate (6.34 g) was added and the mixture stirred for one hour at 25°. The mixture was cooled to 0° and Z—CYCLOHEXYLALA[COCH$_2$Br] (11.2 g) was added. The mixture was allowed to warm to 25° and was stirred for 24 hours. 1N citric acid (20 ml) was added and the mixture extracted with ether/water. The organic phase was washed with water, sodium bicarbonate, and brine. The solvent was dried over sodium sulfate, filtered, and evaporated. The residue was eluted from silica gel with 3:1 hexane/ether to give 14 g of product.

Z—CYCLOHEXYLALA[COCH$_2$]GLY

Z—CYCLOHEXYLALA[COCH$_2$CH(CO$_2$—t—Bu)$_2$] (6.0 g) was dissolved in trifluoroacetic acid (20 ml) and stirred at 25° for three hours. The solvent was evaporated and the residue was dissolved in toluene. The mixture was heated to reflux for three hours. The solution was allowed to cool to 25° and the solvent evaporated. The residue was eluted from silica gel with 3:1 hexane/ethyl acetate to give 3.5 g of product.

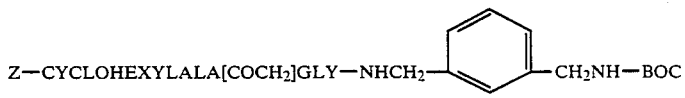

Z—CYCLOHEXYLALAL[COCH$_2$]GLY (3.5 g), BOC-xylylenediamine (2.29 g) and hydroxybenzotriazole (1.31 g) were dissolved in DMF (30 ml) and cooled to 0°. Dicyclohexylcarbodiimide (2.0 g) was added and the mixture was allowed to warm slowly to 25° and stir for 24 hours. The mixture was filtered and the filtrate was extracted with ethyl acetate and water.

The organic phase was washed with water, sodium bicarbonate, and brine. The solvent was dried over sodium sulfate, filtered, and evaporated. The residue was eluted from silica gel with 3:1 hexane/ethyl acetate to give 3.9 g of product.

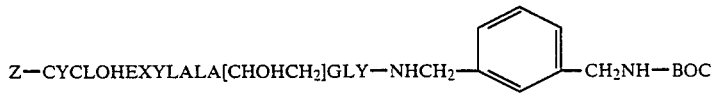

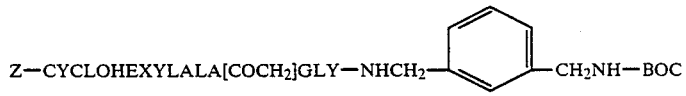

(3.9 g) was dissolved in ethanol (30 ml) and cooled to 0°. Sodium borohydride (0.26 g) was added and the mixture was stirred at 0° for 0.5 hour and at 25° for two hours. Citric acid (1N) was added to destroy any excess hydride reagent. The mixture was extracted with ethyl acetate and water. The organic layer was washed with water, sodium bicarbonate, and filtered and evaporated to give 3.9 g of product.

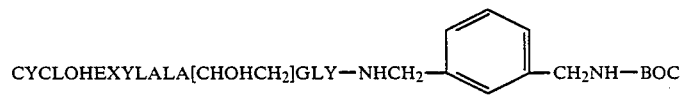

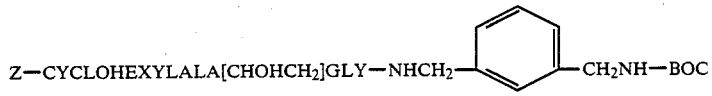
Z—CYCLOHEXYLALA[CHOHCH₂]GLY—NHCH₂—⟨phenyl⟩—CH₂NH—BOC (3.9 g) was dissolved in methanol (30 ml) and palladium on carbon (20%) (0.5 g) was added. The system was evacuated and then flushed with hydrogen from a balloon. The mixture was stirred for four hours at 25°. The system was flushed with nitrogen and the mixture was filtered. The solvent was evaporated to give 3 g of product.

to warm slowly to 25° and stir for 24 hours. The mixture was filtered and the filtrate was extracted with ethyl acetate and water. The organic layer was washed with water, sodium bicarbonate, and brine. The solvent was dried over sodium sulfate, filtered, and evaporated. The residue was eluted from silica gel with 1:1 ethyl acetate/hexane then ethyl acetate to give (0.8 g) of product.

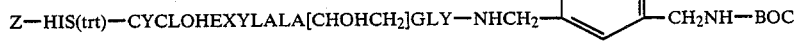
Z—HIS(trt)—CYCLOHEXYLALA[CHOHCH₂]GLY—NHCH₂—⟨phenyl⟩—CH₂NH—BOC

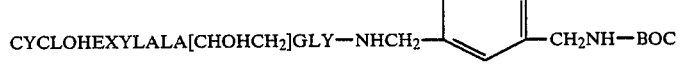
CYCLOHEXYLALA[CHOHCH₂]GLY—NHCH₂—⟨phenyl⟩—CH₂NH—BOC (3 g), Z—HIS(TRT) (3.6 g), and hydroxybenzotriazole (0.91 g) were dissolved in DMF (30 ml) and cooled to 0°. Dicyclohexylcarbodiimide (1.4 g) was added and the mixture was allowed to warm slowly to 25° and stir for 24 hours. The mixture was filtered and the filtrate was extracted with ethyl acetate and water. The organic phase was washed with water, sodium bicarbonate, and brine. The solvent was dried over sodium sulfate, filtered, and evaporated. The residue was eluted from silica gel with 1:1 ethyl acetate/hexane to give 4.9 g of product.

INTERMEDIATES FOR EXAMPLE 13

Z—CYCLOHEXYLALA[COCH₂]LEU[(CO₂-t-Bu)₂]

Sodium hydride (1.3 g) (50% in mineral oil) was washed with hexane and then suspended in DMSO (50 ml). Z—CYCLOHEXYLALA[COCH₂CH(CO₂-t-Bu)₂] (14 g) in DMSO (50 ml) was added. The mixture was stirred at 25° until hydrogen evolution stopped (one hour). The mixture was cooled to 5° and isobutyl iodide (3.11 ml) was added. The mixture was allowed to warm to 25° and stir for 24 hours. 1N citric acid (20 ml) was

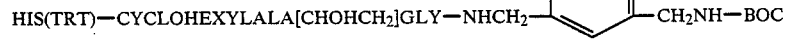
HIS(TRT)—CYCLOHEXYLALA[CHOHCH₂]GLY—NHCH₂—⟨phenyl⟩—CH₂NH—BOC

Z—HIS(TRT)—CYCLOHEXYLALA[CHOHCH₂]GLY—NHCH₂—⟨phenyl⟩—CH₂NH—BOC (4.9 g) was dissolved in methanol (40 ml) and palladium on carbon (20%) (0.4 g) was added. The system was flushed with hydrogen from a balloon and the mixture was stirred for four hours at 25°. The system was then flushed with nitrogen and the mixture was filtered. The solvent was evaporated to give 4 g of product.

added and the mixture was extracted with ether/water. The organic layer was washed with water, sodium bicarbonate, and brine. The solvent was dried over sodium sulfate, filtered, and evaporated. The residue was eluted from silica gel with 4:1 hexane/ether to get 9.0 g of product which was dissolved in dichloromethane and

DNMA—HIS(TRT)—CYCLOHEXYLALA[CHOHCH₂]GLY—NHCH₂—⟨phenyl⟩—CH₂NH—BOC

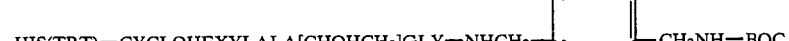
HIS(TRT)—CYCLOHEXYLALA[CHOHCH₂]GLY—NHCH₂—⟨phenyl⟩—CH₂NH—BOC (1 g), di-(α-naphthylmethyl)acetic acid (0.39 g), and hydroxybenzotriazole (0.15 g) were mixed together in DMF (15 ml) and cooled to 0°. Dicyclohexylcarbodiimide (0.23 g) was added and the mixture was allowed evaporated.
Calcd. for $C_{33}H_{51}NO_7 \cdot 0.5CH_2Cl_2$: C, 65.33; H, 8.51; N, 2.27. Found: C, 65.67; H, 8.46; N, 2.64.

Z—CYCLOHEXYLALA[COCH₂]LEU

Z—CYCLOHEXYLALA[COCH₂]LEU[(CO₂-t-Bu)₂] (9.0 g) was dissolved in trifluoroacetic acid (15 ml) and stirred at 25° for three hours. The solvent was evaporated and the residue was dissolved in toluene (70 ml). The mixture was heated to reflux for three hours.

hours. Citric acid (1N) was added to destroy any excess hydride and the mixture was extracted with ethyl acetate and water. The organic phase was washed with water, sodium bicarbonate, and brine. The solvent was dried over sodium sulfate, filtered, and evaporated. The residue was eluted from silica gel with dichloromethane and then ethyl acetate to give 6 g of product.

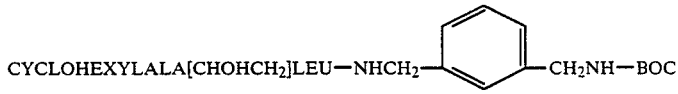

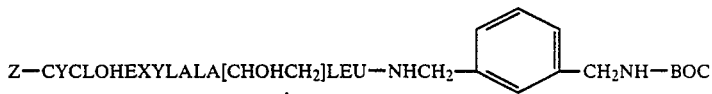

The mixture was allowed to cool to 25° and the solvent was then evaporated. The residue was eluted from silica gel with 3:1 hexane/ethyl acetate to give 4.5 g of product.

(6 g) was dissolved in methanol (50 ml) and palladium on carbon (20%) (0.5 g) was added. The system was evacuated and then flushed with hydrogen from a balloon. The mixture was stirred for six hours at 25°. The

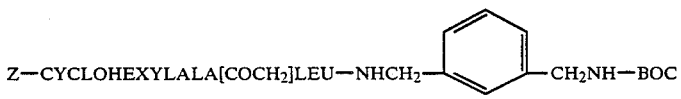

Z-CYCLOHEXYLALA[COCH₂]LEU (4.5 g), BOC-xylylenediamine (2.55 g), and hydroxybenzotriazole (1.46 g) were dissolved in DMF (50 ml) and system was flushed with nitrogen and the mixture was filtered. The solvent was evaporated to give 4.8 g of product.

cooled to 0°. Dicyclohexylcarbodiimide (2.22 g) was added and the mixture was allowed to warm slowly to 25° and stir for 24 hours. The mixture was filtered and the filtrate was extracted with ethyl acetate and water. The organic layer was washed with water, sodium bicarbonate, and brine. The solvent was dried over sodium sulfate, filtered, and evaporated. The residue was eluted from silica gel with 4:1 hexane/ethyl acetate to give 6.0 g of product.

(4.8 g), Z—HIS(TRT) (5.03 g), and hydroxybenzotriazole (1.3 g) were dissolved in DMF (30 ml) and cooled to 0°. Dicyclohexylcarbodiimide (2.0 g) was added and the mixture was allowed to warm slowly to 25° and stir for 24 hours. The mixture was filtered and the filtrate was extracted with ethyl acetate and water. The organic phase was washed with water, sodium bicarbonate, and brine. The organic phase was dried over sodium sulfate, filtered, and evaporated. The resi-

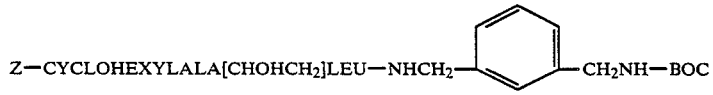

(6 g) was dissolved in ethanol (40 ml) and cooled to 0°. Sodium borohydride (0.36 g) was added and the mixture was stirred at 0° for one hour and at 25° for two due was eluted from silica gel with ethyl acetate to give 5.5 g of product.

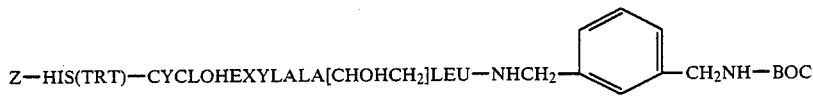

(5.5 g) was dissolved in methanol (30 ml) and palladium on carbon (20%) (0.4 g) was added. The system was flushed with hydrogen from a balloon and stirred for four hours. The system was then flushed with nitrogen and the mixture was filtered. The solvent was evaporated to give 5 g of product.

due was eluted from silica gel with 15% ethyl acetate/hexane to give 0.8 g of product.

CYCLOHEXYLALA[CHOHCH₂]LEU-NHCH₂Ph

BOC—CYCLOHEXYLALA[CHOHCH₂]LEU-NHCH₂Ph (0.8 g) was dissolved in dichloromethane

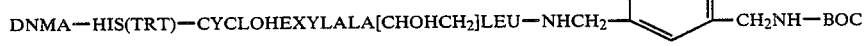

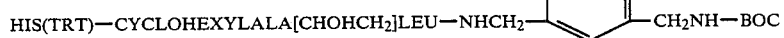

(1.0 g), di-(α-naphthylmethyl)acetic acid (0.39 g), and hydroxybenzotriazole (0.15 g) were dissolved in DMF and cooled to 0°. Dicyclohexylcarbodiimide (0.23 g) was added and the mixture was allowed to warm slowly to 25° and was stirred for 24 hours. The mixture was filtered and the filtrate was extracted with ethyl acetate and water. The organic layer was washed with water, sodium bicarbonate, and brine. The solvent was dried over sodium sulfate, filtered, and evaporated. The residue was eluted from silica gel with 1:1 ethyl acetate/hexane then ethyl acetate to give 0.8 g of product.

INTERMEDIATES FOR EXAMPLE 14

BOC—CYCLOHEXYLALA[COCH₂]LEU—NHCH₂Ph

BOC—CYCLOHEXYLALA[COCH₂]LEU (1.3 g), benzylamine (0.36 g), and hydroxybenzotriazole (0.45 g) were stirred together in dimethylformamide (20 ml). The mixture was cooled to 0° and dicyclohexylcarbodiimide (0.7 g) added. The mixture was allowed to warm slowly to 25° and was stirred for 24 hours. The mixture was filtered and the filtrate extracted with ethyl acetate and water. The organic phase was washed with water, sodium bicarbonate, and brine. The extract was dried over sodium sulfate, filtered, and evaporated. The residue was eluted from silica gel with 20% ethyl acetate/hexane to give 1.6 g of product.

BOC—CYCLOHEXYLALA[CHOHCH₂]LEU—NHCH₂Ph

BOC-CYCLOHEXYLALA[COCH₂]LEU-NHCH₂Ph (1.6 g) was dissolved in ethanol (25 ml) and cooled to 0°. Sodium borohydride (0.13 g) was added and the mixture allowed to warm to 25°. The mixture was stirred for two hours and then acetic acid and water 1:1 was added. The solvent was evaporated and the residue extracted with ethyl acetate and sodium carbonate. The organic phase was washed with brine, dried over sodium sulfate, filtered, and evaporated. The resiand trifluoroacetic acid (4 ml) added. The mixture was stirred for one hour at 25° and then the solvent was evaporated. The residue was extracted with ethyl acetate and sodium carbonate. The organic phase was washed with brine, dried over sodium sulfate, filtered, and evaporated to give 0.6 g of product.

Z—HIS(TRT)-CYCLOHEXYLALA[CHOHCH₂]LEU—CHCH₂Ph

CYCLOHEXYLALA[CHOHCH₂]LEU—NHCH₂Ph (0.6 g), Z—HIS(TRT) (0.9 g), and hydroxybenzotriazole (0.23 g) were stirred together in dimethylformamide (15 ml). The mixture was cooled to 0° and dicyclohexylcarbodiimide (0.35 g) added. The mixture was allowed to warm slowly to 25° and was stirred for 24 hours. The mixture was filtered and the filtrate extracted with ethyl acetate and water. The organic phase was washed with water, sodium bicarbonate, and brine. The extract was dried over sodium sulfate, filtered, and evaporated. The residue was eluted from silica gel with 1:4 hexane/ethyl acetate to give 1.1 g of product.

HIS(TRT)—CYCLOHEXYLALA[CHOHCH₂]LEU—NHCH₂Ph

Z—HIS(TRT)—CYCLOHEXYLALA[CHOHCH₂]LEU—NHCH₂Ph (1.3 g) was dissolved in methanol (20 ml) and palladium on carbon (20%) (0.2 g) added. The flask was flushed with hydrogen and the mixture stirred for three hours. The flask was flushed with nitrogen and the mixture filtered. The solvent was evaporated to give 1.0 g of product.

DNMA—HIS(TRT)—CYCLOHEXYLALA[CHOHCH₂]LEU—NHCH₂Ph

HIS(TRT)—CYCLOHEXYLALA[CHOHCH₂]LEU—NHCH₂Ph (0.5 g), di-(α-naphthylmethyl)acetic acid (0.23 g), and hydroxybenzotriazole (0.1 g) were stirred together in dimethylformamide (15 ml). The mixture was cooled to 0° and dicyclohexylcarbodiimide (0.14 g) was added. The mixture was allowed to warm slowly to 25° and stir for 24 hours. The mixture was filtered and the filtrate extracted with ethyl acetate and water. The organic layer was washed with water, sodium bicarbonate, and brine. The extract was dried over sodium sulfate, filtered, and evaporated. The residue was eluted from silica gel with 80:20 ethyl acetate/hexane to give 0.5 g of product.

INTERMEDIATES FOR EXAMPLE 15

BOC—CYCLOHEXYLALA[COCH$_2$-]LEU—NHCH$_2$CH(CH$_3$)CH$_2$CH$_3$

BOC—CYCLOHEXYLALA[COCH$_2$]LEU (1.2 g), (S)-2-methylbutylamine (0.37 ml), and hydroxybenzotriazole (0.42 g) were stirred together in dimethylformamide (20 ml). The mixture was cooled to 0° and dicyclohexylcarbodiimide (0.65 g) was added. The mixture was allowed to warm slowly to 25° and was stirred for 24 hours. The mixture was filtered and the filtrate extracted with ethyl acetate and water. The organic phase was washed with water, sodium bicarbonate, and brine. The extract was dried over sodium sulfate, filtered, and evaporated. The residue was eluted from silica gel with 10% ethyl acetate/hexane to give 1.8 g of product.

BOC—CYCLOHEXYLALA[CHOHCH$_2$-]LEU—NHCH$_2$CH(CH$_3$)CH$_2$CH$_3$

BOC—CYCLOHEXYLALA[COCH$_2$-]LEU—NHCH$_2$CH(CH$_3$)CH$_2$CH$_3$ (1.8 g) was dissolved in ethanol and cooled to 0°. Sodium borohydride (0.15 g) was added and the mixture was allowed to warm to 25° and stir for two hours. Acetic acid and water (1:1) were added and the solvent was evaporated. The residue was extracted with ethyl acetate and sodium carbonate. The organic phase was washed with brine, dried over sodium sulfate, filtered, and evaporated. The residue was eluted from silica gel with 15% ethyl acetate/hexane to give 1 g of product.

CYCLOHEXYLALA[CHOHCH$_2$-]LEU—NHCH$_2$CH(CH$_3$)CH$_2$CH$_3$

BOC—CYCLOHEXYLALA[CHOHCH$_2$-]LEU—NHCH$_2$CH(CH$_3$)CH$_2$CH$_3$ (0.9 g) was dissolved in dichloromethane and trifluoroacetic acid (4 ml) was added. The mixture was stirred for one hour at 25° then the solvent was evaporated. The residue was extracted with ethyl acetate and sodium carbonate. The organic layer was washed with brine, dried over sodium sulfate, filtered, and evaporated to give 0.7 g of product.

Z—HIS(TRT)—CYCLOHEXYLALA[CHOHCH$_2$-]LEU—NHCH$_2$CH(CH$_3$)CH$_2$CH$_3$

CYCLOHEXYLALA[CHOHCH$_2$-]LEU—NHCH$_2$CH(CH$_3$)CH$_2$CH$_3$ (0.7 g), Z—HIS(TRT) (1.1 g), and hydroxybenzotriazole (0.27 g) were stirred together in dimethylformamide (15 ml). The mixture was cooled to 0° and dicyclohexylcarbodiimide (0.41 g) was added. The mixture was allowed to warm slowly to 25° and was stirred for 24 hours. The mixture was filtered and the filtrate was extracted with ethyl acetate and water. The organic phase was washed with water, sodium bicarbonate, and brine. The extract was dried over sodium sulfate, filtered, and evaporated. The residue was eluted from silica gel with 1:4 hexane/ethyl acetate to give 0.5 g of product.

HIS(TRT)—CYCLOHEXYLALA[CHOHCH$_2$-]LEU—NHCH$_2$CH(CH$_3$)CH$_2$CH$_3$

Z—HIS(TRT)—CYCLOHEXYLALA[CHOHCH$_2$]LEU—NHCH$_2$CH—(CH$_3$)CH$_2$CH$_3$ (0.5 g) was dissolved in ethanol and 20% palladium on carbon (0.1 g) was added. The flask was flushed with hydrogen and stirred for three hours. The flask was then flushed with nitrogen and the mixture filtered. The solvent was evaporated to give 0.4 g of product.

DNMA—HIS(TRT)—CYCLOHEXYLALA[CHOHCH$_2$]LEU—NHCH$_2$CH(CH$_3$)CH$_2$CH$_3$

HIS(TRT)—CYCLOHEXYLALA[CHOHCH$_2$-]LEU—NHCH$_2$CH(CH$_3$)—CH$_2$CH$_3$ (0.4 g), di-($\alpha$-naphthylmethyl)acetic acid (0.2 g), and hydroxybenzotriazole (0.1 g) were stirred in dimethylformamide (15 ml). The mixture was cooled to 0° and dicyclohexylcarbodiimide (0.12 g) was added. The mixture was allowed to warm slowly to 25° and was stirred for 24 hours. The mixture was filtered and the filtrate extracted with ethyl acetate and water. The organic phase was washe with water, sodium bicarbonate, and brine. The extract was dried over sodium sulfate, filtered, and evaporated. The residue was eluted from silica gel with 1:1 ethyl acetate/hexane to give 0.4 g of product.

INTERMEDIATES FOR EXAMPLE 16

BOC—CYCLOHEXYLALA[COCH$_2$]-GLY—NHCH$_2$CH(CH$_3$)CH$_2$CH$_3$

BOC—CYCLOHEXYLALA[COCH$_2$]GLY (1.9 g), 2-methylbutylamine (0.69 ml), and hydroxybenzotriazole (0.78 g) were stirred together in dimethylformamide (15 ml) and cooled to 0°. Dicyclohexylcarbodiimide (1.19 g) was added and the mixture allowed to warm to 25° and stir overnight. The mixture was filtered and the filtrate extracted with ethyl acetate and water. The organic phase was washed with water, sodium bicarbonate, and brine. The extract was dried over sodium sulfate, filtered, and evaporated. The residue was eluted from silica gel with 1:1 ether/hexane to give 1.5 g of product.

BOC—CYCLOHEXYLALA[CHOHCH$_2$]-GLY—NHCH$_2$CH(CH$_3$)CH$_2$CH$_3$

BOC—CYCLOHEXYLALA[COCH$_2$]-GLY—NHCH$_2$CH(CH$_3$)CH$_2$CH$_3$ (1.5 g) was dissolved in ethanol (15 ml) and cooled to 0°. Sodium borohydride (0.14 g) was added and the mixture allowed to warm to 25° and stir for three hours. Acetic acid and water 1:1 was added and the solvent evaporated. The residue was extracted with ethyl acetate and sodium bicarbonate. The extract was washed with brine, dried over sodium sulfate, filtered, and evaporated. The residue was eluted from silica gel with 1:1 ethyl acetate/hexane to give 1.25 g of product, mp 115°–125°.

CYCLOHEXYLALA[CHOHCH$_2$]-GLY—NHCH$_2$CH(CH$_3$)CH$_2$CH$_3$

BOC—CYCLOHEXYLALA[CHOHCH$_2$]-GLY—NHCH$_2$CH(CH$_3$)CH$_2$CH$_3$ (1.25 g) was dissolved in dichloromethane (20 ml) and trifluoroacetic acid (4 ml) added. The mixture was stirred for two hours at 25° and then the solvent was evaporated. The residue was extracted with ethyl acetate and sodium carbonate. The organic phase was washed with brine, dried over sodium sulfate, filtered, and evaporated to give 1.0 g of product.

Z—HIS(TRT)—CYCLOHEXYLALA[CHOHCH₂]-GLY—NHCH₂CH(CH₃)CH₂CH₃

CYCLOHEXYLALA[CHOHCH₂]-GLY—NHCH₂CH(CH₃)CH₂CH₃ (1.0 g), Z—HIS(TRT) (1.67 g), and hydroxybenzotriazole (0.42 g) were stirred together in dimethylformamide (15 ml) and cooled to 0°. Dicyclohexylcarbodiimide (0.65 g) was added and the mixture allowed to warm to 25° slowly. The mixture was stirred for 24 hours and then filtered. The filtrate was extracted with ethyl acetate and water. The organic phase was washed with water, sodium bicarbonate, and brine. The extract was dried over sodium sulfate, filtered, and evaporated. The residue was eluted from silica gel with ethyl acetate to give 1.9 g of product.

HIS(TRT)—CYCLOHEXYLALA[CHOHCH₂]-GLY—NHCH₂CH(CH₃)C₂CH₃

Z—HIS(TRT)—CYCLOHEXYLALA[-CHOHCH₂]GLY—NHCH₂CH—(CH₃)CH₂CH₃ (1.9 g) was dissolved in methanol and palladium on carbon (20%) (0.2 g) added. The flask was flushed with hydrogen. The mixture was stirred for seven hours at 25°. The flask was flushed with nitrogen and the mixture filtered. The solvent was evaporated to give 1.6 g of product.

DNMA—HIS(TRT)—CYCLOHEXYLALA[-CHOHCH₂]GLY—NHCH₂CH(CH₃)CH₂CH₃

HIS(TRT)—CYCLOHEXYLALA[CHOHCH₂]-GLY—NHCH₂CH(CH₃)—CH₂CH₃ (0.8 g), di-(α-naphthylmethyl)acetic acid (0.4 g), and hydroxybenzotriazole (0.16 g) were stirred together in dimethylformamide (20 ml) and cooled to 0°. Dicyclohexylcarbodiimide (0.24 g) was added and the mixture was allowed to warm slowly to 25°. The mixture was stirred for 24 hours and then filtered. The filtrate was extracted with ethyl acetate and water. The organic phase was washed with water, sodium bicarbonate, and brine. The extract was dried over sodium sulfate, filtered, and evaporated. The residue was eluted from silica gel with ethyl acetate to give 0.85 g of product.

INTERMEDIATES FOR EXAMPLE 17

BOC—CYCLOHEXYLALA[COCH₂]-GLY—NHCH₂Ph

BOC—CYCLOHEXYLALA[COCH₂]GLY (1.2 g), benzylamine (0.32 g), and hydroxybenzotriazole (0.4 g) were stirred together in dimethylformamide (20 ml). The mixture was cooled to 0° and dicyclohexylcarbodiimide (0.62 g) added. The mixture was allowed to warm to 25° and stir for 24 hours. The mixture was filtered and the filtrate extracted with ethyl acetate and water. The organic layer was washed with water, sodium bicarbonate, and brine. The extract was dried over sodium sulfate, filtered, and evaporated. The residue was eluted from silica gel with 4:1 hexane/ethyl acetate to give 1 g of product.

BOC—CYCLOHEXYLALA[CHOHCH₂]-GLY—NHCH₂Ph

BOC—CYCLOHEXYLALA[COCH₂]-GLY—NHCH₂Ph (1.5 g) was dissolved in ethanol (20 ml) and cooled to 0°. Sodium borohydride (0.14 g) was added and the mixture stirred for two hours at 25°. Acetic acid and water 1:1 was added to quench the reaction and the solvent evaporated. The residue was extracted with ethyl acetate and sodium bicarbonate. The organic layer was washed with brine, dried over sodium sulfate, filtered, and evaporated to give 1.4 g of product.

CYCLOHEXYLALA[CHOHCH₂]GLY—NHCH₂Ph

BOC—CYCLOHEXYLALA[CHOHCH₂]-GLY—NHCH₂Ph (1.4 g) was dissolved in dichloromethane (15 ml). Trifluoroacetic acid (2 ml) was added and the mixture stirred at 25° for two hours. The solvent was evaporated and the residue extracted with sodium bicarbonate and ethyl acetate. The organic layer was washed with brine, dried over sodium sulfate, filtered, and evaporated to give 1.1 g of product.

Z—HIS(TRT)—CYCLOHEXYLALA[CHOHCH₂]-GLY—NHCH₂Ph

CYCLOHEXYLALA[CHOHCH₂]-GLY—NHCH₂Ph (1.1 g), Z-HIS(TRT) (1.78 g), and hydroxybenzotriazole (0.5 g) were stirred together in dimethylformamide (20 ml). The mixture was cooled to 0° and dicyclohexylcarbodiimide (0.7 g) added. The mixture was allowed to warm to 25° slowly and was then stirred for 24 hours. The mixture was filtered and the filtrate extracted with ethyl acetate and water. The organic layer was washed with water, sodium bicarbonate, and brine. The extract was dried over sodium sulfate, filtered, and evaporated. The residue was eluted from silica gel with ethyl acetate to give 1.6 g of product.

HIS(TRT)—CYCLOHEXYLALA[CHOHCH₂]-GLY—NHCH₂Ph

Z—HIS(TRT)—CYCLOHEXYLALA[-CHOHCH₂]GLY-NHCH₂Ph (1.6 g) was dissolved in methanol (20 ml) and palladium on carbon (20%) (0.2 g) added. The flask was flushed with hydrogen and stirred for four hours. The flask was then flushed with nitrogen and the mixture filtered. The solvent was evaporated to give 1.3 g of product.

DNMA—HIS(TRT)—CYCLOHEXYLALA[-CHOHCH₂]GLY—NHCH₂Ph

HIS(TRT)—CYCLOHEXYLALA[CHOHCH₂]-GLY—NHCH₂Ph (0.8 g), di-(α-naphthylmethyl)acetic acid (0.33 g), and hydroxybenzotriazole (0.13 g) were stirred together in dimethylformamide (10 ml). The mixture was cooled to 0° and dicyclohexylcarbodiimide (0.2 g) was added. The mixture was allowed to warm slowly to 25° and was stirred overnight. The mixture was filtered and the filtrate extracted with ethyl acetate and water. The organic layer was washed with water, sodium bicarbonate, and brine. The extract was dried over sodium sulfate, filtered, and evaporated. The residue was eluted from silica gel with ethyl acetate to give 0.9 g of product.

INTERMEDIATES FOR EXAMPLES 18 AND 19

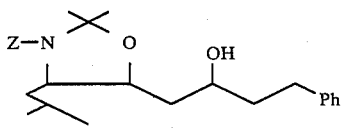

(2-Bromoethyl)benzene (3.05 g, 0.0165 mole) was added to a suspension of 0.40 magnesium turnings in 80 ml anhydrous ethyl ether. The turnings were crused to initiate the reaction. After stirring for two hours the solution was treated dropwise with a solution of

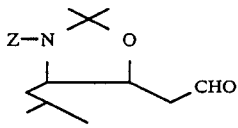

(5.0 g, 0.015 mole) in 50 ml Et₂O. After stirring for two hours, the mixture was diluted to 200 ml with Et₂O, washed with 1N HCl, brine, saturated NaHCO₃ solution, and brine. The organic phase was dried over MgSO₄, filtered, and stripped to an oil, 6.66 g. The oil was chromatographed on silica gel, eluting with 30/70 EtOAc/hexane. The product was recovered as an oil, 4.56 g. Spectral analyses confirmed the structure.

STA[CHOHCH₂]CH₂Ph

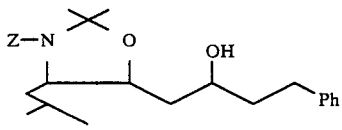

(7.0 g), 0.159 mole) was dissolved in 100 ml of MeOH and 0.47 g of 20% Pd/C catalyst added. The mixture was purged with hydrogen gas for 3.5 hours, filtered, and stripped to 4.59 g of a syrup. NMR analysis confirmed the structure of the product. The material was sufficiently pure to use in the following step.

Z—HIS(TRT)—STA[CHOHCH₂]CH₂Ph

Z—HIS(TRT), (3.99 g, 7.5 mmole) and HOBT.H₂O (1.06 g, 7.88 mmole) were dissolved in 75 ml DMF and cooled to 0°. A solution of dicyclohexylcarbodiimide (1.62 g, 7.88 mmole) in 10 ml DMF was added, followed by a solution of STA[CHOHCH₂]CH₂Ph (1.99 g, 7.5 mmole) in 15 ml DMF. The mixture was stirred and allowed to warm to 25° overnight. The mixture was filtered, and the DMF was removed in vacuo. The residue was dissolved in EtOAc which was washed with 1N citric acid, brine, saturated NaHCO₃, and brine. The organic phase was dried over MgSO, filtered, and stripped to a foam, 5.62 g. The foam was chromatographed on silica gel, eluting with 2/98 MeOH/CHCl₃. The product was separated into 1.5 g of one diastereomer (fast) and 1.8 g of the other (slow). Spectral analyses confirmed the structures of the diastereomers. Each diastereomer was carried on separately in the following synthesis.

HIS(TRT)—STA[CHOHCH₂]CH₂Ph

Z—HIS(TRT)—STA[CHOHCH₂]CH₂Ph (1.39 g, 1.78 mmole, fast isomer) was dissolved in 75 ml MeOH to which was added 0.15 g of 20% Pd/C catalyst. The suspension was purged with hydrogen gas for three hours. The suspension was filtered and stripped to a foam, 1.23 g. Mass spectral analysis confirmed the structure.

Similar treatment of the slow isomer (1.72 g, 2.21 mmole) yielded a white foam, 1.43 g. Mass spectral analysis confirmed the structure.

DNMA—HIS(TRT)—STA[CHOHCH₂]CH₂Ph

Di-(α-naphthylmethyl)acetic acid (0.6 g, 1.78 mmole), HOBT.H₂O (0.25 g, 1.87 mmole) and HIS(TRT)—STA[CHOHCH₂]CH₂Ph (1.15 g, 1.78 mmole, fast isomer) were dissolved in 40 ml DMF. DCC (0.38 g, 1.87 mmole) was added, and the mixture was stirred for four hours at 25°, followed by refrigeration overnight. The mixture was filtered, stripped to an oil in vacuo and taken up into EtOAc. The solution was washed with 1N citric acid, brine, saturated NaHCO₃ solution, and brine. The organic phase was dried over MgSO₄, filtered, and stripped to a foam, 1.74 g. The foam was chromatographed on silica gel, eluting with CHCl₃, and giving a white foam, 1.47 g. Mass spectral analysis confirmed the structure.

Similar treatment of the slow isomer (0.73 g, 2.14 mmole) yielded a white foam, 1.53 g. Mass spectral analysis confirmed the structure.

INTERMEDIATES FOR EXAMPLE 20

Di-(α-NAPHTHYLMETHYL)ACETYL CHLORIDE

Di-(α-naphthylmethyl)acetic acid (8.6 g, 0.025 mole) and 50 ml thionyl chloride were combined and stirred at 25° for 16 hours. The thionyl chloride was removed in vacuo, the residue taken up into hexane, and stripped to an oil. The oil was dissolved in dichloromethane and treated with activated charcoal to remove a dark colored impurity. The mixture was filtered and diluted with hexane. Dichloromethane was gradually removed in vacuo, giving an oily precipitate which was separate from the hexane solution. The hexane solution yielded a crystalline solid which was filtered, washed with hexane and dried to a white solid, 5.95 g. The material was used without further purification.

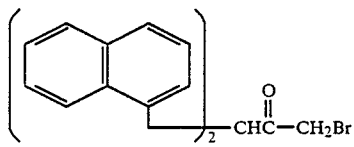

500 ml of an ethereal solution of diazomethane was prepared from 41 g p-tolylsulfonylmethylnitrosamide per Org. Syn. Coll. Vol. 4, pp. 251-3, and cooled to 0°. A solution of di-(α-naphthylmethyl)acetyl chloride (17.3 g, 0.048 mole) in 300 ml 50/50 CH₂Cl₂/Et₂O at −10° was added to the diazomethane solution, and warmed to 20° over two hours. The solution was then purged with anhydrous HBr gas until the solution became acidic to wet litmus. After stirring 45 minutes, the mixture was filtered and stripped to an oil. The oil was dissolved in Et₂O, treated with activated charcoal to remove colored impurities, filtered, and stripped to an oil, 20.5 g. The oil was chromatographed on silica gel eluting with 25/75 EtOAc/hexane, and giving a syrup which slowly crystallized, 18.7 g. NMR analysis confirmed the structure.

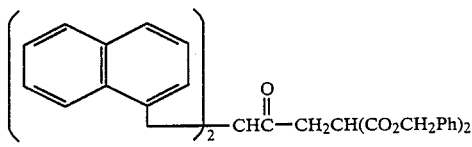

4.3 g of 50% NaH emulsion in oil was washed with dry THF and added to 300 ml dry THF. Dibenzyl malonate (22.4 ml, 0.089 mole) was added with exotherm and gas evolution. After stirring for 45 minutes a solution was obtained, to which was added a solution of

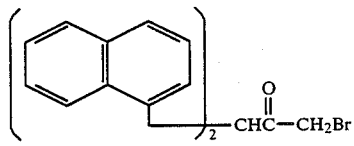

(18.3 g, 0,0438 mole) in 120 ml dry THF. A white precipitate formed, which was stirred at 25° overnight.

10 ml glacial acetic acid was added and the mixture was stripped to a paste. The paste was suspended in EtOAc, washed with 1N citric acid, brine, saturated NaHCO$_3$, and brine. The organic phase was dried over MgSO$_4$, filtered, and stripped to an oil, 40.2 g. Chromatography on silica gel, eluting with a gradient of 5–10% EtOAc in hexane gave 22.77 g of the product as an oil. The material was sufficiently pure to use in the following step.

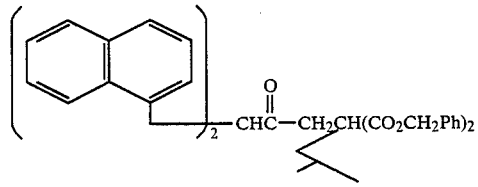

1.11 g (0.023 mole) of 50% NaH emulsion in oil was washed with hexane and added to 25 ml DMSO with stirring. A solution of
(13.6 g, 0.022 mole) in 75 ml DMSO was added, giving an exotherm and gas evolution. After stirring 45 minutes, gas evolution subsided. The mixture was cooled until the solvent began to solidify, and 1-iodo-2-methylpropane (7.6 ml, 0.066 mole) was added. The mixture was allowed to warm to 25° overnight. 100 ml of H$_2$O was added, and pH was adjusted to 4.0 with 1N HCl. The mixture was exhaustively extracted with Et$_2$O and the organic phase was washed with brine, 1N citric acid, brine, saturated NaHCO$_3$, and brine. The organic phase was dried over MgSO$_4$, filtered, and stripped to a yellow syrup, 16.4 g. The syrup was chromatographed on silica gel eluting with 9% EtOAc in hexane. The product was recovered as a syrup, 11.7 g. NMR and mass spectral analyses confirmed the structure.

DNMA[COCH$_2$]LEU (11.2 g, 0.0165 mole) was dissolved in 300 ml 50/50 THF/MeOH, to which was charged 0.50 g of 20% Pd on charcoal catalyst. The solution was purged overnight with hydrogen gas, filtered, and stripped to a foam. The foam was refluxed in 150 ml toluene for 2.5 hours which completed decarboxylation of the intermediate diacid. The solution was treated with activated charcoal, filtered, and stripped to a yellow gum, 7.55 g. NMR and mass spectral analyses confirmed the structure. The material was sufficiently pure for use in the subsequent step.

DNMA[COCH$_2$]LEU—S—TA—NHCH$_2$CH(CH$_3$)CH$_2$CH$_3$

DNMA[COCH$_2$]LEU (3.39 g, 7.5 mmole) and HOBT, (1.06 g, 7.88 mmole) were dissolved in 25 DMF. In a separate flask STA—NHCH$_2$CH(CH$_3$)CH$_2$CH$_3$.HCl (2.17 g, 7.5 mmole) was combined with 20 ml DMF and Et$_3$N (1.3 ml, 9.4 mmole). The solutions were combined, and a third solution of DCC (1.62 g, 7.88 mmole) in 10 ml DMF was added. The mixture was stirred at 25° for two hours, followed by refrigeration at 4° overnight. The DMF was stripped off, the residue taken up into EtOAc, and the solution filtered. The filtrate was washed with 1N citric acid, brine, saturated NaHCO$_3$, and brine. The organic phase was dried over MgSO$_4$, filtered, and stripped to a yellow foam, 4.59 g. The mixture was chromatographed on silica gel, eluting with a gradient of 75/25 hexane/EtOAc to neat EtOAc. Combining the appropriate fractions gave 1.35 g of the product as a foam. NMR and mass spectral analyses confirmed the structure.

COMMON INTERMEDIATES

Z—HIS(TRT)—OCH$_3$

Z—HIS—OCH$_3$ [J. Chem. Soc. Perkin I, 2261 (1979)] (70 g) was dissolved in dichloromethane (500 ml) and cooled to 0°. Triethyl amine (32 ml) and then trityl chloride (64.3 g) were added. The mixture was allowed to warm to 25° and stir for 24 hours. The mixture was washed with sodium bicarbonate and brine, dried over sodium sulfate, filtered, and evaporated. The residue was crystallized from ethyl acetate to give 100 g of product.

Z—HIS(TRT)

Z—HIS(TRT)—OCH$_3$ (30 g) was dissolved in 300 ml of dioxane and cooled to 0°. Sodium hydroxide (2.7 g) in 80 ml of water was added. The mixture was stirred for one hour and then acidified with 1N citric acid to pH 2. The mixture was extracted with ethyl acetate. The organic phase was washed with brine, dried over sodium sulfate, filtered, and evaporated to give the 27 g of product.

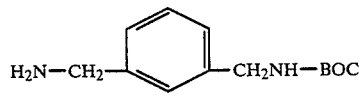

Meta-xylylenediamine (3.0 g) was dissolved in dichloromethane (20 ml) and cooled to 0°, BOC—ON (5.4 g) was added and the mixture allowed to warm to 25° and stir for 24 hours. The solvent was evaporated and the residue was extracted with ethyl acetate/citric acid. The aqueous phase was made basic with 10% sodium hydroxide. The mixture was extracted with ethyl acetate and the organic phase was washed with brine, dried over sodium sulfate, filtered, and evaporated to give 2.9 g of product.

We claim:
1. A pharmaceutical composition comprising a renin-inhibitory effective amount of a compound selected from the group consisting of:
DNMA—HIS—LEU[CHOHCH$_2$]SO$_2$NHCH$_2$Ph,
DNMA—HIS—LEU[CHOHCH$_2$]SO$_2$NHCH$_2$CH$_2$Ph (ISOMER),
DNMA—HIS—STA—LEU

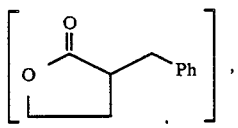

DNMA—HIS—STA—[CH$_2$SO$_2$](CH$_2$)$_3$CH$_3$
DNMA—HIS—CYCLOHEXYLALA[CHOHCH$_2$(CH$_2$)$_2$CH(CH$_3$)$_2$,
DNMA—HIS—CYCLOHEXYLALA[CHOHCH$_2$(CH$_2$)$_5$CH$_3$, DNMA—HIS—CYCLOHEXYLALA[CHOHCHOH]CH$_2$OH,
DNMA—HIS[CH$_2$NH]-STA—NHCH$_2$CH(CH$_3$)CH$_2$CH$_3$, DNMA—HIS[CH$_2$N(BOC)]CH$_2$CH(CH$_3$)CH$_2$CH$_3$,
DNMA—HIS—STA[CH$_2$NH]CH$_2$CH(CH$_3$)CH$_2$CH$_3$,
DNMA—HIS—CYCLOHEXYLALA[CHOHCH$_2$]GLY—LEU—NHCH$_2$Ph,

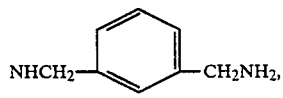

DNMA—HIS—CYCLOHEXYLALA[CHOHCH$_2$]LEU—NHCH$_2$Ph,
DNMA—HIS—CYCLOHEXYLALA[CHOHCH$_2$]LEU—NHCH$_2$CH(CH$_3$)CH$_2$CH$_3$,
DNMA—HIS—CYCLOHEXYLALA[CHOHCH$_2$]GLY—NHCH$_2$CH(CH$_3$)CH$_2$CH$_3$,
DNMA—HIS—CYCLOHEXYLALA[CHOHCH$_2$]GLY—NHCH$_2$Ph, DNMA—HIS—STA[CHOHCH$_2$]CH$_2$Ph, DNMA—HIS—STA]CHOHCH$_2$]CH$_2$Ph (ISOMER), or DNMA—[CHOHCH$_2$]LEU—STA—NHCH$_2$CH(CH$_3$)CH$_2$CH$_3$
together with a pharmaceutically acceptable carrier.

2. A method of treating renin-associated hypertension which comprises administering to a mammal a pharmaceutical composition as claimed in claim 1.

3. A peptide named DNMA—HIS—LEU[CHOHCH]SO$_2$NHCH$_2$Ph, or DNMA—HIS—LEU[CHOHCH$_2$]SO$_2$NHCH$_2$Ph (isomer).

4. A peptide named DNMA—HIS—STA—LEU

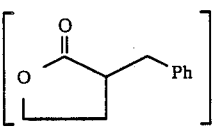

5. A peptide named DNMA—HIS—STA[CH$_2$SO$_2$](CH$_2$)$_3$CH$_3$.
6. A peptide named DNMA—HIS—CYCLOHEXYLALA[CHOHCH$_2$](CH$_2$)$_2$CH(CH$_3$)$_2$.
7. A peptide named DNMA—HIS—CYCLOHEXYLALA[CHOHCH$_2$](CH$_2$)$_5$CH$_3$.
8. A peptide named DNMA—HIS—CYCLOHEXYLALA[CHOHCHOH]CH$_2$OH.
9. A peptide named DNMA—HIS—[CH$_2$NH]-STA—NHCH$_2$CH(CH$_3$)CH$_2$CH$_3$.
10. A peptide named DNMA—HIS—STA[CH$_2$N(BOC)]CH$_2$CH(CH$_3$)CH$_2$CH$_3$.
11. A peptide named DNMA—HIS—STA[CH$_2$NH]CH$_2$CH(CH$_3$)CH$_2$CH$_3$.
12. A peptide named DNMA—HIS—CYCLOHEXYLALA[CHOHCH$_2$]GLY—LEU—NHCH$_2$Ph.
13. A peptide named DNMA—HIS—CYCLOHEXYLALA[CHOHCH$_2$]GLY-

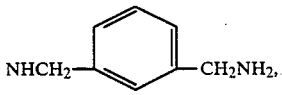

14. A peptide named DNMA—HIS—CYCLOHEXYLALA[CHOHCH$_2$]LEU-

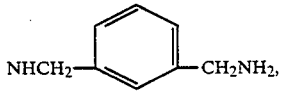

15. A peptide named DNMA—HIS—CYCLOHEXYLALA[CHOHCH$_2$]LEU—NHCH$_2$Ph.
16. A peptide named DNMA—HIS—CYCLOHEXYLALA[CHOHCH$_2$]LEU—NHCH$_2$CH(CH$_3$)CH$_2$CH$_3$.
17. A peptide named DNMA—HIS—CYCLOHEXYLALA[CHOHCH$_2$]-GLY—NHCH$_2$CH(CH$_3$)CH$_2$CH$_3$.
18. A peptide named DNMA—HIS—CYCLOHEXYLALA[CHOHCH$_2$]GLY—NHCH$_2$Ph.
19. A peptide named DNMA—HIS—STA[CHOHCH$_2$]CH$_2$Ph or DNMA—HIS—STA[CHOHCH$_2$]CH$_2$Ph (ISOMER).
20. A peptide named DNMA—HIS—[CHOHCH$_2$]LEU—STA—NHCH$_2$CH(CH$_3$)CH$_2$CH$_3$.

* * * * *

UNITED STATES PATENT AND TRADEMARK OFFICE
CERTIFICATE OF CORRECTION

PATENT NO. : 4,863,905
DATED : September 5, 1989
INVENTOR(S) : Hudspeth, et al

It is certified that error appears in the above-identified patent and that said Letters Patent is hereby corrected as shown below:

Column 67, after line 30 add -- DNMA-HIS-CYCLOHEXYLALA[CHOHCH$_2$]GLY- --.

Column 67, after line 35 add -- DNMA-HIS-CYCLOHEXYLALA[CHOHCH$_2$]LEU- --.

Column 68, line 2 should read -- CHOHCH$_2$]SO$_2$NHCH$_2$Ph, or DNMA-HIS-LEU[-

Column 68, line 35 delete "," and insert -- . --.

Column 68, line 43 delete "," and insert -- . --.

Signed and Sealed this

Twenty-eighth Day of August, 1990

Attest:

HARRY F. MANBECK, JR.

Attesting Officer

Commissioner of Patents and Trademarks